(12) United States Patent
Katayama et al.

(10) Patent No.: US 9,360,432 B2
(45) Date of Patent: Jun. 7, 2016

(54) METHOD FOR MEASURING TRIGLYCERIDE IN LOW-DENSITY LIPOPROTEIN

(75) Inventors: Yuki Katayama, Tokyo (JP); Kazuhito Miyauchi, Tokyo (JP); Shizuyo Takada, Tokyo (JP); Tomomi Murakami, Tokyo (JP)

(73) Assignee: KYOWA MEDEX CO., LTD., Tokyo (JP)

( * ) Notice: Subject to any disclaimer, the term of this patent is extended or adjusted under 35 U.S.C. 154(b) by 1641 days.

(21) Appl. No.: 12/090,906

(22) PCT Filed: Oct. 31, 2006

(86) PCT No.: PCT/JP2006/321730
§ 371 (c)(1),
(2), (4) Date: Jul. 22, 2008

(87) PCT Pub. No.: WO2007/052646
PCT Pub. Date: May 10, 2007

(65) Prior Publication Data
US 2009/0226944 A1    Sep. 10, 2009

(30) Foreign Application Priority Data

Oct. 31, 2005 (JP) ................................. 2005-316476
Mar. 30, 2006 (JP) ................................. 2006-095151

(51) Int. Cl.
*G01N 21/78* (2006.01)
*G01N 33/92* (2006.01)
*C12Q 1/44* (2006.01)
*C12Q 1/61* (2006.01)

(52) U.S. Cl.
CPC ........ *G01N 21/78* (2013.01); *C12Q 1/44* (2013.01); *C12Q 1/61* (2013.01); *G01N 33/92* (2013.01); *G01N 2333/918* (2013.01); *G01N 2333/91215* (2013.01)

(58) Field of Classification Search
None
See application file for complete search history.

(56) References Cited

U.S. PATENT DOCUMENTS

| 4,179,334 | A | * | 12/1979 | Esders et al. ............... 435/19 |
| 5,807,696 | A | | 9/1998 | Miyauchi et al. |
| 6,194,164 | B1 | | 2/2001 | Matsui et al. |
| 6,794,157 | B1 | | 9/2004 | Sugiuchi |
| 6,811,994 | B1 | * | 11/2004 | Miyauchi et al. ............... 435/18 |
| 2003/0207342 | A1 | | 11/2003 | Miyauchi |
| 2005/0042703 | A1 | | 2/2005 | Miyauchi et al. |
| 2005/0287619 | A1 | | 12/2005 | Katayama et al. |
| 2006/0014229 | A1 | * | 1/2006 | Katayama ............... C12Q 1/60 435/11 |

FOREIGN PATENT DOCUMENTS

| JP | 2001-231597 | 8/2001 |
| WO | 96/28734 | 9/1996 |
| WO | 98/47005 | 10/1998 |
| WO | 00/17388 | 3/2000 |
| WO | 00/43537 | 7/2000 |
| WO | 00/60112 | 10/2000 |
| WO | 2004/035817 | 4/2004 |
| WO | 2004/087945 | 10/2004 |

OTHER PUBLICATIONS

Fossati, P. et al. Clin. Chem. 28(10):2077-2080 (1982).*
Okada, M. et al. J. Lab. Clin. Med. 132:195-201 (1998).*
"Triton X Surfactants," excerpt from Union Carbide literature, 10 pages, downloaded from www4.mpbio.com on Mar. 9, 2012.*
"Emulgen 709" specification sheet, 1 page, Kao Corporation literature, downloaded from chemical.kao.com on Mar. 9, 2012.*
Okada, M. et al. Clinical Chemistry 51(10):1804 (Aug. 2005).*

* cited by examiner

*Primary Examiner* — Diana B Johannsen
(74) *Attorney, Agent, or Firm* — Fitzpatrick, Cella, Harper & Scinto

(57) ABSTRACT

The present invention provides a method for a simple and accurate measurement of triglycerides in low-density lipoprotein in a sample comprising performing the following steps sequentially:

(i) a step of generating free glycerol by allowing lipoprotein lipase to act on a sample, in an aqueous medium comprising the sample and a specific surfactant such as polyoxyethylene polyoxyalkylene polycyclic phenyl ether; (ii) a step of removing free glycerol present in the reaction solution of the above step (i); (iii) a step of generating free glycerol by allowing lipoprotein lipase to act on the reaction solution from which free glycerol has been removed in step (ii), in the presence of a specific surfactant such as polyoxyethylene polyoxyalkylene alkyl ether; and (iv) a step of measuring free glycerol generated in step (iii), and a kit used for the method.

7 Claims, No Drawings

METHOD FOR MEASURING TRIGLYCERIDE IN LOW-DENSITY LIPOPROTEIN

TECHNICAL FIELD

The present invention relates to a method and a kit for measuring triglycerides in low-density lipoproteins in a sample.

BACKGROUND ART

Lipoproteins in vivo are mainly classified according to its specific gravity into four groups, i.e. high-density lipoproteins (hereinafter abbreviated as HDL), low-density lipoproteins (hereinafter abbreviated as LDL), very-low-density lipoproteins (hereinafter abbreviated as VLDL), and chylomicrons (hereinafter abbreviated as CM).

Lipid composition and types of apoprotein differ for each lipoprotein, and thus their function in vivo differs significantly with one another. Further, there is also an intermediate-density lipoprotein (hereinafter abbreviated as IDL) being intermediate between VLDL and LDL, as a lipoprotein which is generated during metabolism of VLDL to LDL, while it is classified as LDL in a broad sense.

At present, when screening for diagnosing arterial sclerosis in the field of clinical laboratory test, total cholesterol, total triglyceride, HDL cholesterol, apolipoprotein AI, apolipoprotein B, etc. are generally measured. Recently, LDL cholesterol which is said to be highly associated with arteriosclerosis formation is frequently measured instead of total cholesterol. On the other hand, there are many patients showing coronary atherosclerosis lesion while their LDL cholesterol in blood is not high, and it is said that a condition showing adipositas, hypertriglyceridemia, hypertension, and hyperglycemia in combination is a very dangerous clinical condition that might develop coronary artery diseases. Further, it is also reported that the triglycerides level in LDL in blood is associated with arterial diseases more than LDL cholesterol.

General methods for measuring triglycerides in LDL include a method of fractionating and collecting lipoproteins by ultracentrifugation, precipitation method or using immunoreactions, and measuring triglycerides contained therein. However, all the fractionating methods require time and cost, and are very complicated.

As a method measurable with an autoanalyzer without carrying out fractionation, a method comprising removing triglycerides in all lipoproteins except LDL in the first step, and measuring triglycerides in the remaining LDL in the second step is known (patent references 1 and 2). However, there is a problem that in a sample with high triglycerides in VLDL or CM, triglycerides cannot be completely removed in the first step, and the reaction is carried over to the second step, causing a positive impact.

Further, as a method measurable with an autoanalyzer without carrying out operations for fractionation, a method for measuring triglycerides contained in IDL, which is classified as LDL in a broad sense, is known (patent reference 3). However, the method does not measure triglycerides contained in normal LDL, and therefore the method is not appropriate for measuring triglycerides in LDL.

Further, as a method measurable with an autoanalyzer without carrying out fractionation, a method is known for measuring triglycerides in LDL characterized in that an enzyme reaction is carried out in the presence of a block copolymer of propylene oxide and ethylene oxide, particularly a triblock copolymer of polyoxypropylene and polyoxyethylene (patent reference 4).

Patent Reference 1: WO 00/43537
Patent Reference 2: WO 2004/087945
Patent Reference 3: WO 00/60112
Patent Reference 4: Published Japanese Translation of PCT International Publication No. 2002-508519

DISCLOSURE OF THE INVENTION

Problems to be Solved by the Present Invention

The object of the present invention is to provide a method and a reagent for a simple and accurate measurement of triglycerides.

Means for Solving the Problems

The present invention is related to the following [1] to [20].
[1] A method for measuring triglycerides in low-density lipoprotein in a sample, wherein the following steps (i) to (iv) are performed sequentially.
(i) a step of generating free glycerol by allowing lipoprotein lipase to act on the sample, in an aqueous medium comprising the sample and at least one surfactant selected from the group consisting of polyoxyethylene polyoxyalkelene polycyclic phenyl ether, polyoxypropylene polyoxyalkylene polycyclic phenyl ether, polyoxyethylene alkylphenyl ether formaldehyde condensate, and polyoxyethylene polycyclic phenyl ether having a HLB value of 13.0 or higher and 17.0 or lower;
(ii) a step of removing free glycerol present in the reaction solution of the above step (i);
(iii) a step of generating free glycerol by allowing lipoprotein lipase to act on the reaction solution from which free glycerol has been removed in the above step (ii), in the presence of at least one surfactant selected from the group consisting of polyoxyethylene polyoxyalkylene alkyl ether, polyoxypropylene polyoxyalkylene alkyl ether, polyoxyethylene polyoxyalkylene alkylphenyl ether, polyoxypropylene polyoxyalkylene alkylphenyl ether, polyoxyethylene polycyclic phenyl ether condensate, polyoxyethylene alkylphenyl ether sulfate, polyoxyethylene polycyclic phenyl ether sulfate, and polyoxyethylene polycyclic phenyl ether having a HLB value of 9.0 or higher and lower than 13.0; and,
(iv) a step of measuring free glycerol generated in the above step (iii).
[2] The method according to [1], wherein the free glycerol generated in step (i) is generated from triglycerides in high-density lipoprotein.
[3] The method according to [1] or [2], wherein the removal of free glycerol in step (ii) is carried out enzymatically by converting the free glycerol into a component other than a component related to the measurement of free glycerol in step (iv).
[4] The method according to [1] or [2], wherein the removal of free glycerol in step (ii) is performed by generating hydrogen peroxide with a reagent for generating hydrogen peroxide from free glycerol, and then by removing the hydrogen peroxide.
[5] The method for measuring according to [4], wherein the removal of hydrogen peroxide is performed by allowing catalase to act on the hydrogen peroxide, or allowing a peroxidative substance to act on the hydrogen peroxide in the presence of one part of oxidative coupling chromogen.
[6] The method according to any one of [1] to [5], wherein the measurement of free glycerol in step (iv) is performed by generating hydrogen peroxide with a reagent for generating hydrogen peroxide from free glycerol, and then measuring the hydrogen peroxide.

[7] The measuring method according to any one of [4] to [6], wherein the reagent for generating hydrogen peroxide from free glycerol is a reagent comprising glycerol kinase and glycerol 3-phosphate oxidase, or a reagent comprising glycerol oxidase.

[8] The method according to [6] or [7], wherein the measurement of hydrogen peroxide is performed by generating a dye by allowing a peroxidative substance and oxidative coloring-type chromogens to act on the hydrogen peroxide, and measuring the absorbance of the dye.

[9] The method according to any one of [1] to [8], wherein lipoprotein lipase in step (iii) is reacted in the presence of a bile acid derivative.

[10] The method according to [9], wherein the bile acid derivative is at least one substance selected from the group consisting of cholic acid or a salt thereof, taurocholic acid or a salt thereof, glycocholic acid or a salt thereof, lithocholic acid or a salt thereof, deoxycholic acid or a salt thereof, chenodeoxycholic acid or a salt thereof, ursodeoxycholic acid or a salt thereof, 7-oxolithocholic acid or a salt thereof, 12-oxolithocholic acid or a salt thereof, 12-oxochenodeoxycholic acid or a salt thereof, 7-oxodeoxycholic acid or a salt thereof, hyocholic acid or a salt thereof, hyodeoxycholic acid or a salt thereof, dehydrocholic acid or a salt thereof; a compound shown by the general formula (I)

$$R^1-CH_2-CH(R^2)-CH_2-SO_3^- \quad (I)$$

[wherein $R^1$ is 3-(3-cholamidopropyl)dimethylammonio group; $R^2$ is a hydrogen atom or hydroxyl group]; and a compound shown by the general formula (II)

(II)

(wherein X represents a hydrogen atom or hydroxyl group; $R^3$ and $R^4$ may be the same or different, and represent a substituted or unsubstituted alkyl group, or substituted or unsubstituted alkanoyl group).

[11] A kit for measuring triglycerides in low-density lipoprotein in a sample, comprising:
(a) a first reagent comprising at least one surfactant selected from the group consisting of polyoxyethylene polyoxyalkylene polycyclic phenyl ether, polyoxypropylene polyoxyalkylene polycyclic phenyl ether, polyoxyethylene alkylphenyl ether formaldehyde condensate, and polyoxyethylene polycyclic phenyl ether having a HLB value of 13.0 or higher and 17.0 or lower; lipoprotein lipase; and a reagent for removing free glycerol;
(b) a second reagent comprising at least one surfactant selected from the group consisting of polyoxyethylene polyoxyalkylene alkyl ether, polyoxypropylene polyoxyalkylene alkyl ether, polyoxyethylene polyoxyalkylene alkylphenyl ether, polyoxypropylene polyoxyalkylene alkylphenyl ether, polyoxyethylene polycyclic phenyl ether condensate, polyoxyethylene alkylphenyl ether sulfate, polyoxyethylene polycyclic phenyl ether sulfate, and polyoxyethylene polycyclic phenyl ether having a HLB value of 9.0 or higher and lower than 13.0; and a reagent for measuring free glycerol.

[12] The kit according to [11], wherein the at least one surfactant selected from the group consisting of polyoxyethylene polyoxyalkylene polycyclic phenyl ether, polyoxypropylene alkylene polycyclic phenyl ether, polyoxyethylene alkylphenyl ether formaldehyde condensate, and polyoxyethylene polycyclic phenyl ether having a HLB value of 13.0 or higher and 17.0 or lower allows lipoprotein lipase to act on triglycerides in high-density lipoprotein.

[13] The kit according to [11] or [12], wherein the reagent for removing free glycerol is an enzyme converting free glycerol into a component other than a component related to measurement using the reagent for measuring free glycerol.

[14] The kit according to [11] or [12], wherein the reagent for removing free glycerol is a reagent comprising a reagent for generating hydrogen peroxide from glycerol and a reagent for removing hydrogen peroxide.

[15] The kit according to [14], wherein the reagent for removing hydrogen peroxide is a reagent comprising catalase; or a reagent comprising one part of oxidative coupling chromogens and a peroxidative substance.

[16] The kit according to any one of [11] to [15], wherein the reagent for measuring free glycerol is a reagent comprising the reagent for generating hydrogen peroxide from free glycerol and a reagent for measuring hydrogen peroxide.

[17] The kit according to any one of [14] to [16], wherein the reagent for generating hydrogen peroxide from free glycerol is the reagent comprising glycerol kinase and glycerol 3-phosphate oxidase, or the reagent comprising glycerol oxidase.

[18] The kit according to [16] or [17], wherein the reagent for measuring hydrogen peroxide is a reagent comprising a peroxidative substance and oxidative coloring-type chromogens.

[19] The kit according to any one of [11] to [18], wherein the second reagent further comprises a bile acid derivative.

[20] The kit according to [19], wherein the bile acid derivative is at least one substance selected from the group consisting of cholic acid or a salt thereof, taurocholic acid or a salt thereof, glycocholic acid or a salt thereof, lithocholic acid or a salt thereof, deoxycholic acid or a salt thereof, chenodeoxycholic acid or a salt thereof, ursodeoxycholic acid or a salt thereof, 7-oxolithocholic acid or a salt thereof, 12-oxolithocholic acid or a salt thereof, 12-oxochenodeoxycholic acid or a salt thereof, 7-oxodeoxycholic acid or a salt thereof, hyocholic acid or a salt thereof, hyodeoxycholic acid or a salt thereof, dehydrocholic acid or a salt thereof; a compound shown by the general formula (I)

$$R^1-CH_2-CH(R^2)-CH_2-SO_3^- \quad (I)$$

[wherein $R^1$ is 3-(3-cholamidopropyl)dimethylammonio group; $R^2$ is a hydrogen atom or hydroxyl group]; and a compound shown by the general formula (II)

(II)

(wherein X represents a hydrogen atom or hydroxyl group; $R^3$ and $R^4$ may be the same or different, and represent a substituted or unsubstituted alkyl group, or substituted or unsubstituted alkanoyl group).

Effect of the Present Invention

The present invention provides a method and a kit for a simple and accurate measurement of triglycerides in LDL.

BEST MODE OF CARRYING OUT THE INVENTION

Measurement of triglycerides in LDL of the present invention is performed by: allowing lipoprotein lipase to act on a sample in a reaction solution comprising the sample, and at least one surfactant selected from the group consisting of polyoxyethylene polyoxyalkylene polycyclic phenyl ether (hereinafter abbreviated as POE-POA polycyclic phenyl ether), polyoxypropylene polyoxyalkylene polycyclic phenyl ether (hereinafter abbreviated as POP-POA polycyclic phenyl ether), polyoxyethylene alkylphenyl ether formaldehyde condensate (hereinafter abbreviated as POE alkylphenyl ether formaldehyde condensate), and polyoxyethylene polycyclic phenyl ether having a HLB value of 13.0 or higher and 17.0 or lower (hereinafter abbreviated as POE polycyclic phenyl ether); removing free glycerol generated therefrom and free glycerol originally present in the sample; allowing lipoprotein lipase to act on the reaction solution from which free glycerol has been removed, in the presence of at least one surfactant selected from the group consisting of polyoxyethylene polyoxyalkylene alkyl ether (hereinafter abbreviated as POE-POA alkyl ether), polyoxypropylene polyoxyalkylene alkyl ether (hereinafter abbreviated as POP-POA alkyl ether), polyoxyethylene polyoxyalkylene alkylphenyl ether (hereinafter abbreviated as POE-POA alkylphenyl ether), polyoxypropylene polyoxyalkylene alkylphenyl ether (hereinafter abbreviated as POP-POA alkylphenyl ether), polyoxyethylene polycyclic phenyl ether condensate (hereinafter abbreviated as POE polycyclic phenyl ether condensate), polyoxyethylene alkylphenyl ether sulfate (herein abbreviated as POE alkylphenyl ether sulfate), polyoxyethylene polycyclic phenyl ether sulfate (hereinafter abbreviated as POE polycyclic phenyl ether sulfate), and polyoxyethylene polycyclic phenyl ether having a HLB value of 9.0 or higher and lower than 13.0 (hereinafter abbreviated as POE polycyclic phenyl ether) to generate free glycerol and measuring the generated free glycerol.

Hereinafter, polyoxyethylene polyoxyalkylene group will be abbreviated as POE-POA, and polyoxypropylene polyoxyalkylene group will be abbreviated as POP-POA.

Preferred measurement of triglycerides in LDL of the present invention is characterized in that it is performed under a condition where a reaction of triglycerides in VLDL in a sample with lipoprotein lipase is suppressed, or not promoted in any of reaction steps. Thus, the influence of triglycerides caused by VLDL containing triglycerides abundantly on the measurements can be substantially avoided.

Preferred measurement of triglycerides in LDL of the present invention is characterized in that it is performed under a condition where a reaction of triglycerides in VLDL and CM in a sample with lipoprotein lipase is suppressed, or not promoted, in any of the reaction steps. Thus, the influence of triglycerides caused by VLDL and CM comprising triglycerides abundantly on the measurements can be substantially avoided.

A particularly preferred and specific method for measuring triglycerides in LDL of the present invention include a method for selectively measuring triglycerides in LDL comprising: removing triglyceride in HDL and free glyceride in a reaction solution containing at least one surfactant selected from the group consisting of POE-POA polycyclic phenyl ether, POP-POA polycyclic phenyl ether, POE alkylphenyl ether formaldehyde condensate and POE polycyclic phenyl ether having a HLB value of 13.0 or higher and 17.0 or lower, which does not suppress the reaction, or promotes the reaction of triglycerides in HDL with lipoprotein lipase, and which suppresses the reaction, or does not promote the reaction of triglycerides in LDL and VLDL with lipoprotein lipase; allowing lipoprotein lipase to act in the presence of at least one surfactant selected from the group consisting of POE-POA alkyl ether, POP-POA alkyl ether, POE-POA alkylphenyl ether, POP-POA alkylphenyl ether, POE polycyclic phenyl ether condensate, POE alkylphenyl ether sulfate, POE polycyclic phenyl ether sulfate and POE polycyclic phenyl ether having a HLB value of 9.0 or higher and lower than 13.0, which does not suppress the reaction, or promotes the reaction of triglycerides with lipoprotein lipase in LDL, and which suppresses the reaction, or does not promote the reaction of triglycerides in VLDL with lipoprotein lipase.

A particularly preferred and specific method of the present invention for measuring triglycerides in LDL include a method for selectively measuring triglycerides in LDL comprising: removing triglycerides in HDL and free glyceride in a reaction solution containing at least one surfactant selected from the group consisting of POE-POA polycyclic phenyl ether, POP-POA polycyclic phenyl ether, POE alkylphenyl ether formaldehyde condensate and POE polycyclic phenyl ether having a HLB value of 13.0 or higher and 17.0 or lower, which does not suppress the reaction, or may promote the reaction of triglycerides in HDL with lipoprotein lipase, and which suppresses the reaction, or does not promote the reaction of triglycerides in LDL, VLDL and CM with lipoprotein lipase; allowing lipoprotein lipase to act in the presence of at least one surfactant selected from the group consisting of POE-POA alkyl ether, POP-POA alkyl ether, POE-POA alkylphenyl ether, POP-POA alkylphenyl ether, POE polycyclic phenyl ether condensate, POE alkylphenyl ether sulfate, POE polycyclic phenyl ether sulfate and POE polycyclic phenyl ether having a HLB value of 9.0 or higher and lower than 13.0, which does not suppress the reaction, or promotes the reaction of triglycerides in LDL with lipoprotein lipase, and which suppresses the reaction, or does not promote the reaction of triglyceride in VLDL and CM with lipoprotein lipase.

LDL as an object for measurement of the present invention may be either LDL in a broad sense with a specific gravity of 1.006 to 1.063, or LDL in a narrow sense with a specific gravity of 1.019 to 1.063. However, when LDL in a broad sense is an object for measurement, IDL with a specific gravity of 1.006 to 1.019 as well as so-called VLDL remunant, which is a part of lipoprotein particles and is a lipoprotein particles having the same specific gravity as IDL, are encompassed in a measuring object.

A sample used in the present invention includes whole blood, plasma, serum, spinal fluid, saliva, amniotic fluid, urine, sweat, pancreatic fluid and the like, and plasma and serum are preferred.

A lipoprotein lipase used in the present invention is not specifically limited as long as it is an enzyme having an activity of hydrolyzing triglyceride in lipoprotein, and includes lipoprotein lipase obtained from, for example, animals, plants or microorganisms, and lipoprotein lipase produced by genetic engineering techniques. Further, cholesterol ester-hydrolyzing enzymes having an activity of hydrolyzing triglycerides in lipoprotein etc. are encompassed in lipoprotein lipase of the present invention.

Chemically modified lipoprotein lipases may also be used as a lipoprotein lipase. Further, commercially available ones may also be used.

Commercially available lipoprotein lipases include cholesterol esterase "Amano" 3 (CHE3; Amano Enzyme, Inc.), cholesterol esterase (CEBP-M; Asahi Kasei Corporation), lipoprotein lipase (LPL311: Toyobo Co., Ltd.), lipoprotein lipase "Amano" 6 (LPL6; Amano Enzyme, Inc.), lipoprotein lipase "Amano" 3 (LPL3; Amano Enzyme, Inc.), EST "Amano" 2 (Amano Enzyme, Inc.), lipoprotein lipase (LPBP; Asahi Kasei Corporation), cholesterol esterase [COE313 (chemically modified cholesterol esterase); Toyobo Co., Ltd.].

As a group modifying the enzyme in the chemical modification of lipoprotein lipase (chemically-modifying group), for example, a group having polyethylene glycol as a main component, a group having polypropylene glycol as a main component, a group having a copolymer of polypropylene glycol and polyethylene glycol, a group comprising soluble polysaccharides, a sulfopropyl group, sufobutyl group, polyurethane group, a group having a chelating function can be exemplified, and a group having polyethylene glycol as a main component is preferred. Soluble polysaccharides include for example, dextran, pullulan, and soluble starch.

As a reagent for chemically modifying lipoprotein lipase (chemically-modifying agent), a compound having the above-mentioned chemically-modifying group together with a functional group or a structure that can react with an amino group, carboxyl group, sulfhydryl group or the like of the enzyme can be exemplified. As a functional group or a structure that can react with an amino group of the enzyme, for example, a carboxyl group, an active ester group (N-hydroxysuccinimide group, etc.), an acid anhydride, an acid chloride, an aldehyde, an epoxide group, 1,3-propanesultone, 1,4-butanesultone or the like can be exemplified. As a functional group or a structure that can react with a carboxyl group of the enzyme, for example, an amino group can be exemplified. As a group or a structure that can react with a sulfhydryl group of the enzyme, a maleimide group, a disulfide, and an α-haloester such as α-iodoester can be exemplified.

As a chemically-modifying agent, commercially available ones can be used. As a commercially available chemically-modifying agent, SUNBRITE VFM-4101, SUNBRITE ME-050AS and SUNBRITE DE-030AS, which have a group having polyethylene glycol as a main component and N-hydroxysuccinimide group (all produced by NOF Corporation); SUNBRITE AKM series (for example SUNBRITE AKM-1510), SUNBRITE ADM series and SUNBRITE ACM series, which have a group comprising polyalkylene glycol as a main component and an acid anhydride structure (all produced by NOF Corporation); EPOX-3400 and M-EPOX-5000 which have a group having polyethylene glycol as a main component and an epoxide group (both produced by Sheawater Polymers); diethylenetriamine-N,N,N',N'',N''-pentaacetic dianhydride which has a group having a chelating function and an acid anhydride structure (DTPA anhydride; Dojindo Laboratories) can be exemplified.

Chemical modification of lipoprotein lipase can be performed, for example, by the following method, but is not limited to this method. First, the enzyme is dissolved in a buffer solution of pH 8.0 or higher (for example HEPES buffer solution), and 0.01 to 500-fold molar amounts of a chemically-modifying agent is added thereto at 0 to 55° C., and the mixture is stirred for 5 minutes to 5 hours. In the actual enzyme reaction, not only the reaction solution itself, but a solution from which unreacted chemically-modifying agents, and the like are removed with an ultrafilter, and the like. according to need can also be used as a chemically modified enzyme.

Concentration of lipoprotein lipase used in the present invention is not specifically limited as long as the measurement of triglycerides in LDL can be performed. Its concentration in the reaction mixture is preferably 0.01 to 400 U/mL, and more preferably 0.02 to 200 U/mL. Further, two or more kinds of lipoprotein lipase can be used in combination in the present invention.

Polyoxyalkylene in POE-POA polycyclic phenyl ether used in the present invention includes polyoxypropylene, polyoxybutylene and the like other than polyoxyethylene.

Polyoxyalkylene in POP-POA polycyclic phenyl ether used in the present invention, includes polyoxyethylene, polyoxybutylene and the like other than polyoxypropylene.

Degree of polymerization of oxyethylene in polyoxyethylene in POE-POA polycyclic phenyl ether and degree of polymerization of oxypropylene in polyoxypropylene in POP-POA polycyclic phenyl ether are preferably 2 to 60, and more preferably 4 to 30. Degree of polymerization of oxyalkylene in polyoxyalkylene is preferably 1 to 40, and more preferably 1 to 20.

Polymerization style of POE-POA in POE-POA polycyclic phenyl ether and that of POP-POA in POP-POA polycyclic phenyl ether used in the present invention are not specifically limited, and include block polymerization and random polymerization. Block polymerization includes diblock copolymer, triblock copolymer, and tetrablock copolymer.

Specific examples (products) of POE-POA polycyclic phenyl ether include Newcol 2608F, Newcol 2600FB (all produced by Nippon Nyukazai Co. Ltd.), New Calgen GP120, New Calgen CP15-150 (all produced by Takemoto Oil & Fat, Co. Ltd.).

Degree of polymerization of oxyethylene in polyoxyethylene in POE alkylphenyl ether formaldehyde condensate used in the present invention is preferably 1 to 60, and more preferably 2 to 30. Alkyl of POE alkylphenyl ether formaldehyde condensate includes a straight-chain or branched alkyl having 6 to 30 carbon atoms, such as hexyl, heptyl, octyl, isooctyl, nonyl, decyl, undecyl, dodecyl (lauryl), tridecyl, tetradecyl (myristyl), pentadecyl, hexadexyl (cetyl), heptadecyl, octadecyl (stearyl), nonadecyl, icosyl, heneicosyl, docosyl (behenyl), tricosyl, tetracosyl, pentacosyl, hexacosyl, heptacosyl, octacosyl, nonacosyl, and triacontyl.

Specific examples (products) of POE alkylphenyl ether formaldehyde condensate include NIKKOL R1020 (Nikko Chemicals Co., Ltd.).

Degree of polymerization of oxyethylene in polyoxyethylene in POE polycyclic phenyl ether having a HLB value of 13.0 or higher and 17.0 or lower used in the present invention is preferably 1 to 60, and more preferably 2 to 30. Polycyclic phenyl in POE polycyclic phenyl ether having a HLB value of 13.0 or higher and 17.0 or lower includes a phenyl group substituted with two or more groups (substituents) each having one aromatic ring in the group or a phenyl group substituted with one or more groups (substituents) each having two or more aromatic rings in the group. The group having one aromatic ring in the group includes benzyl, 1-(phenyl)ethyl and the like. The group having two or more aromatic rings in the group includes naphthyl and the like. HLB values of POE polycyclic phenyl ether having a HLB value of 13.0 or higher and 17.0 or lower, are preferably 13.1 or higher and 15 or lower, and particularly preferably 13.2 or higher and 14 or lower.

Specific examples (products) of POE polycyclic phenyl ether having a HLB value of 13.0 or higher and 17.0 or lower include Emulgen B66 (HLB 13.2; produced by Kao Corporation); Newcol 610 (HLB 13.8; produced by Nippon Nyukazai Co., Ltd.); Newcol 710 (HLB 13.6; produced by Nippon Nyukazai Co., Ltd.); Emulgen A-90 (HLB 14.5; produced by Kao Corporation); BLAUNON TSP-50 (HLB 16.9; produced by Aoki Oil Industrial Co., Ltd.); Newcol 714 (HLB 15.0; produced by Nippon Nyukazai Co., Ltd.); Newcol 2614 (HLB 15.0; produced by Nippon Nyukazai Co., Ltd.); Newcol 2609 (HLB 13.0; produced by Nippon Nyukazai Co., Ltd.); New Calgen CP120 (HLB 13.0; produced by Takemoto Oil & Fat, Co. Ltd.).

Concentration of POE-POA polycyclic phenyl ether, POP-POA polycyclic phenyl ether, POE alkylphenyl ether formaldehyde condensate and POE polycyclic phenyl ether having a HLB value of 13.0 or higher and 17.0 or lower used in the present invention is not specifically limited as long as the reaction of triglycerides in HDL can proceed, and its concentration in the reaction solution is preferably 0.01 to 10%, and more preferably 0.02 to 5%. Further, two or more kinds of these compounds can be used in combination in the present invention.

Polyoxyalkylene in POE-POA alkyl ether used in the present invention includes polyoxypropylene, polyoxybutylene and the like other than polyoxyethylene.

Polyoxyalkylene in POP-POA alkyl ether used in the present invention includes polyoxyethylene, polyoxybutylene and the like other than polyoxypropylene.

Degree of polymerization of oxyethylene in polyoxyethylene in POE-POA alkyl ether and degree of polymerization of oxypropylene in polyoxyprolylene in POP-POA alkyl ether are preferably 2 to 60, and more preferably 4 to 30. Degree of polymerization of oxyalkylene in polyoxyalkylene is preferably 1 to 40, and more preferably 1 to 20.

Alkyl in POE-POA alkyl ether and POP-POA alkyl ether includes a straight-chain or branched alkyl having 6 to 30 carbon atoms, such as hexyl, heptyl, octyl, isooctyl, nonyl, decyl, undecyl, dodecyl (lauryl), tridecyl, tetradecyl (myristyl), pentadecyl, hexadexyl (cetyl), heptadecyl, octadecyl (stearyl), nonadecyl, icosyl, heneicosyl, docosyl (behenyl), tricosyl, tetracosyl, pentacosyl, hexacosyl, heptacosyl, octacosyl, nonacosyl, and triacontyl.

Polymerization style of POE-POA in POE-POA alkyl ether and that of POP-POA in POP-POA alkyl ether used in the present invention are not specifically limited, and include block polymerization and random polymerization. Block polymerization includes diblock copolymer, triblock copolymer, and tetrablock copolymer.

Specific examples (products) of POE-POA alkyl ether include Wondersurf S1400 and Wondersurf RL100 (both produced by Aoki Oil Industrial Co., Ltd.).

Polyoxyalkylene in POE-POA alkylphenyl ether used in the present invention includes polyoxypropylene, polyoxybutylene and the like other than polyoxyethylene.

Polyoxyalkylene in POP-POA alkylphenyl ether used in the present invention include polyoxyethylene, polyoxybutylene and the like other than polyoxypropylene.

Degree of polymerization of oxyethylene in polyoxyethylene in POE-POA alkylphenyl ether and degree of polymerization oxypropylene in polyoxypropylene in POP-POA alkylphenyl ether are preferably 2 to 60, and more preferably to 30. Degree of polymerization of oxyalkylene in polyoxyalkylene is preferably 1 to 40, and more preferably 1 to 20.

Alkyl in POE-POA alkylphenyl ether and POP-POA alkylphenyl ether includes a straight-chain or branched alkyl having 6 to 30 carbon atoms, such as hexyl, heptyl, octyl, isooctyl, nonyl, decyl, undecyl, dodecyl (lauryl), tridecyl, tetradecyl (myristyl), pentadecyl, hexadexyl (cetyl), heptadecyl, octadecyl (stearyl), nonadecyl, icosyl, heneicosyl, docosyl (behenyl), tricosyl, tetracosyl, pentacosyl, hexacosyl, heptacosyl, octacosyl, nonacosyl, and triacontyl.

Polymerization style of POE-POA in POE-POA alkylphenyl ether and that of POP-POA in POP-POA alkylphenyl ether used in the present invention are not specifically limited, and include block polymerization and random polymerization. Block polymerization include diblock copolymer, triblock copolymer, and tetrablock copolymer.

Specific examples (products) of POE-POA alkylphenyl ether include Emulgen L40 (produced by Kao Corporation).

Degree of polymerization of oxyethylene in polyoxyethylene in POE polycyclic phenyl ether condensate used in the present invention is preferably 1 to 60, and more preferably 2 to 30.

Polycyclic phenyl in POE polycyclic phenyl ether condensate includes a phenyl group substituted with two or more groups (substituents) each having one aromatic ring in the group, or a phenyl group substituted with one or more groups (substituents) each having two or more aromatic rings in the group. The group having one aromatic ring in the group includes benzyl, 1-(phenyl)ethyl, and the like. The group having two or more aromatic rings in the group includes naphthyl, and the like.

Specific examples (products) of POE polycyclic phenyl ether condensate include New Calgen E150 (Takemoto Oil & Fat, Co. Ltd.), and the like.

Degree of polymerization of oxyethylene in polyoxyethylene in POE alkylphenyl ether sulfate used in the present invention is preferably 1 to 60, and more preferably 2 to 30.

Alkyl of POE alkylphenyl ether sulfate includes a straight-chain or branched alkyl having 6 to 30 carbon atoms, such as hexyl, heptyl, octyl, isooctyl, nonyl, decyl, undecyl, dodecyl (lauryl), tridecyl, tetradecyl (myristyl), pentadecyl, hexadexyl (cetyl), heptadecyl, octadecyl (stearyl), nonadecyl, icosyl, heneicosyl, docosyl (behenyl), tricosyl, tetracosyl, pentacosyl, hexacosyl, heptacosyl, octacosyl, nonacosyl, and triacontyl.

Specific examples (products) of polyoxyethylene alkylphenyl ether sulfate include HI-TENOL N08 (produced by Dai-ichi Kogyo Seiyaku Co., Ltd.).

Degree of polymerization of oxyethylene in polyoxyethylene in POE polycyclic phenyl ether sulfate used in the present invention is preferably 1 to 60, and more preferably 2 to 30.

Polycyclic phenyl in POE polycyclic phenyl ether sulfate includes a phenyl group substituted with two or more groups (substituents) each having one aromatic ring in the group, or a phenyl group substituted with one or more groups (substituents) each having two or more aromatic rings in the group. The group having one aromatic ring in the group includes benzyl, 1-(phenyl)ethyl, and the like. The group having two or more aromatic rings in the group includes naphthyl, and the like.

Specific examples (products) of POE polycyclic phenyl ether sulfate include Newcol 707SF (produced by Nippon Nyukazai Co., Ltd.).

Degree of polymerization of oxyethylene in polyoxyethylene in POE polycyclic phenyl ether having a HLB value of 9.0 or higher and lower than 13.0 used in the present invention is preferably 1 to 60, and more preferably 2 to 30. Polycyclic phenyl in POE polycyclic phenyl ether having a HLB value of 9.0 or higher and lower than 13.0 includes a phenyl group substituted with two or more groups (substituents) each having one aromatic ring in the group, or a phenyl group substituted with one or more groups (substituents) each having two or more aromatic rings in the group. The group having one aromatic ring in the group includes benzyl, 1-(phenyl)ethyl, and the like. The group having two or more aromatic rings in the group includes naphthyl, and the like. HLB values of POE polycyclic phenyl ether having a HLB value of 9.0 or higher and lower than 13.0 is preferably 10 or higher and 12.9 or lower, and more preferably 11 or higher and 12.8 or lower.

Polycyclic phenyl in POE polycyclic phenyl ether having a HLB value of 9.0 or higher and lower than 13.0 includes a phenyl group substituted with two or more groups (substituents) each having one aromatic ring in the group, or a phenyl group substituted with one or more groups (substituents) each having two or more aromatic rings in the group. The group having one aromatic ring in the group includes benzyl, 1-(phenyl)ethyl, and the like. The group having two or more aromatic rings in the group includes naphthyl, and the like.

Specific examples (products) of POE polycyclic phenyl ether having a HLB value of 9.0 or higher and lower than 13.0 include Emulgen A60 (HLB 12.8; produced by Kao Corporation); BLAUNON DSP12.5 (HLB 12.7; produced by Aoki Oil Industrial Co., Ltd.); BLAUNON TSP20 (HLB 12.7; produced by Aoki Oil Industrial Co., Ltd.); BLAUNON DSP-9 (HLB 11.4; produced by Aoki Oil Industrial Co., Ltd.); BLAUNON DSP-7.5 (HLB 9.2; produced by Aoki Oil Industrial Co., Ltd.); BLAUNON TSP-16 (HLB 12.7; produced by Aoki Oil Industrial Co., Ltd.).

Concentration of POE-POA alkyl ether, POP-POA alkyl ether, POE-POA alkylphenyl ether, POP-POA alkylene alkylphenyl ether, POE polycyclic phenyl ether condensate, POE alkylphenyl ether sulfate, POE polycyclic phenyl ether sulfate, and POE polycyclic phenyl ether having a HLB value of 9.0 or higher and lower than 13.0 used in the present invention is not specifically limited as long as reaction of triglycerides in LDL can be performed, and the concentration in the reaction solution is preferably 0.01 to 10%, and more preferably 0.02 to 5%. Further, two or more kinds of these may be used in combination in the present invention.

HLB values means a hydrophilic-lipophilic balance value. HLB values of POE polycyclic phenyl ether used in the present invention can be calculated by the methods described in "Surfactant Handbook" (Tokiyuki Yoshida et al; Kogyo Tosho), "New surfactant" (Hiroshi Horiguchi; Sankyo Shuppan). Further, HLB values described in manufacturer's catalogues or brochures of various surfactants can also be used.

Bile acid derivatives used in the present invention are not limited as long as measurement of triglycerides in LDL can be performed, and includes bile acid derivatives having an anionic surfactant activity, bile acid derivatives having an amphoteric surfactant activity, and bile acid derivatives having a non-ionic surfactant activity.

Bile acid derivatives having an anionic surfactant activity include cholic acid or a salt thereof, taurocholic acid or a salt thereof, glycocholic acid or a salt thereof, lithocholic acid or a salt thereof, deoxycholic acid or a salt thereof, chenodeoxycholic acid or a salt thereof, ursodeoxycholic acid or a salt thereof, 7-oxolithocholic acid or a salt thereof, 12-oxolithocholic acid or a salt thereof, 12-oxochenodeoxicholic acid or a salt thereof, 7-oxodeoxycholic acid or a salt thereof, hyocholic acid or a salt thereof, hyodeoxycholic acid or a salt thereof, dehydrocholic acid or a salt thereof, and the like. Salt includes ammonium salt, lithium salt, sodium salt, potassium salt, magnesium salt, calcium salt, and the like.

Bile acid derivatives having an amphoteric surfactant activity include a compound shown by general formula (I)

$$R^1-CH_2-CH(R^2)-CH_2-SO_3^-$$ (I)

(wherein $R^1$ represents 3-(3-cholamidopropyl)dimethylammonio group; and $R^2$ represents a hydrogen atom or hydroxyl group) (hereinafter referred to as compound (I)). Hereinafter a compound (I) wherein $R^2$ is a hydrogen atom will be referred to as CHAPS, and a compound (I) wherein $R^2$ is a hydroxyl group will be referred to as CHAPSO.

Bile acid derivatives having a non-ionic surfactant activity include a compound shown by general formula (II)

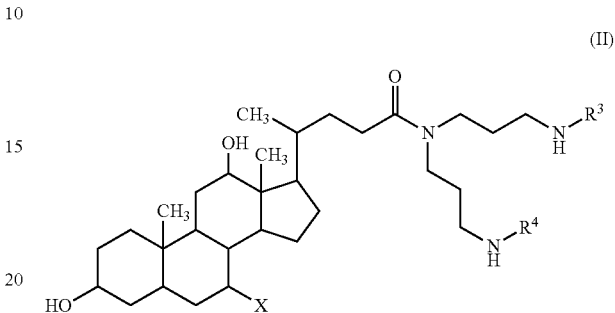

(wherein X represents a hydrogen atom or hydroxyl group; $R^3$ and $R^4$ may be the same or different, and represent a substituted or unsubstituted alkyl, or a substituted or unsubstituted alkanoyl) (hereinafter referred to as compound (II)). Alkyl in alkyl, alkanoyl includes a straight-chain or branched alkyl having 1 to 10 carbon atoms, such as methyl, ethyl, propyl, isopropyl, butyl, isobutyl, sec-butyl, tert-butyl, pentyl, neopentyl, hexyl, heptyl, octyl, nonyl, and decyl. Substituent of substituted alkyl and substituted alkanoyl includes hydroxyl group, halogen atom, and the like. Halogen atom means each atom of fluorine, chlorine, bromine and iodine.

Among compounds (II), a compound wherein $R^3$ and $R^4$ are both

COCH(OH)CH(OH)CH(OH)CH(OH)CH$_2$OH (hereinafter referred to as substituent A) is preferred. Hereinafter, a compound wherein X, $R^3$ and $R^4$ are respectively a hydrogen atom, substituent A and substituent A is referred to as deoxy-BIGCHAP, and a compound wherein X, $R^3$ and $R^4$ are respectively a hydroxyl group, substituent A and substituent A will be referred to as BIGCHAP.

Concentration of bile acid derivatives used in the present invention is not specifically limited as measurement of triglycerides in LDL can be performed, and the concentration in the reaction solution is 0.001 to 10%, and more preferably 0.01 to 1%. In the present invention, two or more kinds of bile acid derivatives may be used.

A reaction solution used for measurement of triglycerides in LDL of the present invention includes deionized water, distilled water, buffer solution, and the like, and buffer solution is preferred. Buffer used for buffer solution includes tris(hydroxymethyl)aminomethane buffer, phosphate buffer, borate buffer and Good's buffer.

Good's buffer includes 2-morpholinoethanesulfonic acid (MES), bis(2-hydroxyethyl)iminotris(hydroxymethyl)methane (Bis-Tris), N-(2-acetoamido)iminodiacetate (ADA), piperazine-N,N'-bis(2-ethanesulfonic acid) (PIPES), N-(2-acetoamido)-2-aminoethane sulfonic acid (ACES), 3-morpholino-2-hydroxypropanesulfonic acid (MOPSO), N,N-bis(2-hydroxyethyl)-2-aminoethanesulfonic acid (BES), 3-morpholinopropanesulfonic acid (MOPS), N-[tris(hydroxymethyl)methyl]-2-aminoethanesulfonic acid (TES), 2-[4-(2-hydroxyethyl)-1-piperazinyl]ethanesulfonic acid (HEPES), 3-[N,N-bis(2-hydroxyethyl)amino]-2-hydroxypropanesulfonic acid (DIPSO), N-[tris(hydroxymethyl)methyl]-2-hydroxy-3-aminopropanesulfonic acid (TAPSO), piperazine-N,N'-bis(2-hydroxypropanesulfonic acid) (POPSO), 3-[4-(2-hydroxyethyl)-1-piperazinyl]-2-hydroxypropanesulfonic acid (HEPPSO), 3-[4-(2-hydroxyethyl)-1-piperazinyl]propanesulfonic acid [(H)EPPS], N-[tris(hydroxymethyl)methyl]glycine (Tricine), N,N-bis(2-hydroxyethyl)glycine (Bicine), N-tris(hydroxymethyl)methyl-3-aminopropanesulfonic acid (TAPS), N-cyclohexyl-2-aminoethanesulfonic acid (CHES), N-cyclohexyl-3-amino-2-hydroxypropanesulfonic acid (CAPSO), N-cyclohexyl-3-aminopropanesulfonic acid (CAPS). Concentration of buffer solution is not specifically limited as long as it is suitable for measurement, and is preferably 0.001 to 2.0 mol/L, and more preferably 0.005 to 1.0 mol/L.

Measurement of triglycerides in LDL of the present invention can be performed by the sequential steps as follows.
(i) a step of generating a free glycerol by allowing lipoprotein lipase to act on a sample in a reaction solution comprising the sample and at least one surfactant selected from the group consisting of POE-POA polycyclic phenyl ether, POP-POA polycyclic phenyl ether, POE alkylphenyl ether formaldehyde condensate, and POE polycyclic phenyl ether having a HLB value of 13.0 or higher and 17.0 or lower;
(ii) a step of removing free glycerol present in the reaction solution of the above step (i);
(iii) a step of generating a free glycerol by allowing lipoprotein lipase to act on the reaction solution from which free glycerol has been removed in the above step (ii), in the presence of at least one surfactant selected from the group consisting of POE-POA alkyl ether, POP-POA alkyl ether, POE-POA alkylphenyl ether, POP-POA alkylphenyl ether, POE polycyclic phenyl ether condensate, POE alkylphenyl ether sulfate, POE polycyclic phenyl ether sulfate and POE polycyclic phenyl ether having a HLB value of 9.0 or higher and lower than 13.0;
(iv) a step of measuring free glycerol generated in the above step (iii).

Reaction temperature of the reaction in each step is for example 10 to 50° C., and preferably 20 to 40° C. Reaction time is 1 to 20 min, and preferably 2 to 10 min. Steps (i) and (ii), and steps (iii) and (iv) can be performed at the same time, respectively.

Removal of free glyceride present in the reaction solution in step (ii) can be performed by converting enzymatically free glycerol into a component other than a component related to the measurement of the generated free glycerol in step (iv). The method for removing free glycerol in step (ii) can be suitably selected by a person skilled in the art, in combination with the method for measuring free glyceride in step (iv).

Removal of free glycerol can be performed by a method comprising generating hydrogen peroxide by allowing a reagent for generating hydrogen peroxide from free glycerol to act on a free glycerol, and removing the generated hydrogen peroxide. The method for measuring free glycerol in step (iv) when using the removing method includes a method comprising generating hydrogen peroxide by allowing a reagent for generating hydrogen peroxide from free glycerol to act on a free glycerol, and measuring the generated hydrogen peroxide.

A reagent for generating hydrogen peroxide from free glycerol includes a reagent comprising glycerol kinase and glycerol-3-phosphate oxidase, and a reagent comprising glycerol oxidase.

A glycerol kinase of the present invention is not specifically limited as long as it is an enzyme having an activity of converting glycerol into glycerol 3-phosphate in the presence of ATP. For example, a glycerol kinase obtained from animals, plants or microorganisms, and glycerol kinase produced by genetic engineering techniques can be used. Further, commercially available ones such as glycerol kinase (GYK-301; Toyobo Co., Ltd.), glycerol kinase (GYK-311, Toyobo Co., Ltd.), glycerol kinase (GYK-311, Toyobo Co., Ltd.) and glycerol kinase (GKZ; Asahi Kasei Corporation) can be used.

Glycerol kinase may be an unmodified enzyme or a chemically modified enzyme. Chemically modified glycerol kinase can be prepared, for example, by the above-mentioned chemical modification method by using the above-mentioned chemically-modifying agents.

Concentration of glycerol kinase used in the present invention is not particularly limited as long as measurement of triglycerides in LDL can be performed, and the concentration in the reaction solution is preferably 0.1 to 20 U/mL, and more preferably 0.2 to 10 U/mL. Further, two or more kinds of glycerol kinases can be used in combination in the present invention.

Glycerol-3-phosphate oxidase in the present invention is not particularly limited as long as it is an enzyme having an ability of generating hydrogen peroxide from glycerol 3-phosphate. For example, glycerol-3-phosphate oxidase obtained from animals, plants or microorganisms as well as that produced by genetic engineering techniques. Commercially available ones such as L-α-glycerophosphoric acid oxidase (G30-301, Toyobo Co., Ltd.), L-α-glycerophosphoric acid oxidase (GPOM, Toyobo Co., Ltd.), L-α-glycerophosphoric acid oxidase (GPOSP; Asahi Kasei Corporation) can be also used.

Glycerol-3-phosphate oxidase may be an unmodified enzyme or a chemically modified enzyme. Chemically modified glycerol-3-phosphate oxidase can be prepared, for example, with the above-mentioned chemical modification method by using the above-mentioned chemically-modifying agents.

Concentration of glycerol-3-phosphate oxidase used in the present invention is not particularly limited as long as measurement of triglycerides in LDL can be performed, and the concentration in the reaction solution is preferably 1 to 60 U/mL, and more preferably 2 to 30 U/mL. Further, two or more kinds of glycerol-3-phosphate oxidase can be used in combination in the present invention.

Glycerol oxidase of the present invention is not particularly limited as long as it is an enzyme having an activity of generating hydrogen peroxide from glycerol. For example, glycerol oxidase obtained from animals, plants, or microorganisms as well as that produced by genetic engineering techniques can be used. Further, commercially available ones can also be used. Glycerol oxidase may be an unmodified enzyme or a chemically modified enzyme. Chemically modified glycerol-3-phosphate oxidase can be prepared with the above-mentioned chemical modification method by using for example the above-mentioned chemically-modifying agents. Concentration of glycerol oxidase used in the present invention is not particularly limited as long as measurement of triglycerides in LDL can be performed, and the concentration in the reaction solution is preferably 1 to 400 U/mL, and more preferably 2 to 200 U/mL. Further, two or more kinds of glycerol oxidases can be used in combination in the present invention.

Hydrogen peroxide generated from free glycerol by using a reagent for generating hydrogen peroxide from free glycerol according to the above-mentioned method can be removed by using a reagent for removing hydrogen peroxide. Examples of the reagent for removing hydrogen peroxide include: a reagent comprising catalase; a peroxidative substance such as peroxidase and one part of oxidative coupling-type chromogens, that is a hydrogen donors such as phenols or anilines, or a coupler such as 4-aminoantipyrine. When using a reagent comprising catalase as the reagent for removing hydrogen peroxide, hydrogen peroxide can be removed by allowing catalase to act to the hydrogen peroxide in the first step, and converting the hydrogen peroxide into water and hydrogen. When using a peroxidative substance such as peroxidase and one part of oxidative coupling-type chromogens as a reagent for removing hydrogen peroxide, hydrogen peroxide can be removed by allowing the hydrogen peroxide to act on one part of oxidative coupling-type chromogens in the presence of the peroxidative substance to give a colorless substance.

Concentration of catalase when using a reagent comprising catalase as a reagent for removing hydrogen peroxide is not particularly limited as long as removal of hydrogen peroxide derived from triglycerides in HDL and free glycerol can be performed, and the concentration in the reaction solution is preferably 50 to 4000 U/mL, and more preferably 100 to 2000 U/mL.

When using the combination of a peroxidative substance such as peroxidase and one part of oxidative coupling type chromogens as a reagent for removing hydrogen peroxide, the concentration of the peroxidative substance is not specifically limited as long as it is a concentration that a colorless substance can be generated from a reaction of the peroxidative substance with hydrogen peroxide derived from triglyceride in HDL and free glycerol. When peroxidase is used as a peroxidative substance, the concentration of peroxidase is preferably 1 to 100 U/mL in the reaction solution, and more preferably 2 to 50 U/mL.

Examples of couplers include 4-aminoantipyrine (4-AA), 3-methyl-2-benzothiazolinone hydrazone.

Examples of phenol-type of hydrogen donors include phenol, 4-chlorophenol, 3-methylphenol, 3-hydroxy-2,4,6-tri-iodobenzoic acid (HTIB).

Examples of aniline-type of hydrogen donors include:
N-(3-sulfopropyl)aniline,
N-ethyl-N-(2-hydroxy-3-sulfopropyl)-3-methylaniline (TOOS),
N-ethyl-N-(2-hydroxy-3-sulfopropyl)-3,5-dimethylaniline (MAOS),
N-ethyl-N-(2-hydroxy-3-sulfopropyl)-3,5-dimethoxyaniline (DAOS),
N-ethyl-N-(3-sulfopropyl)-3-methylaniline (TOPS),
N-(2-hydroxy-3-sulfopropyl)-3,5-dimethoxyaniline (HDAOS),
N,N-dimethyl-3-methylaniline, N,N-di(3-sulfopropyl)-3,5-dimethoxyaniline,
N-ethyl-N-(3-sulfopropyl)-3-methoxyaniline, N-ethyl-N-(3-sulfopropyl)aniline,
N-ethyl-N-(3-sulfopropyl)-3,5-dimethoxyaniline, N-(3-sulfopropyl)-3,5-dimethoxyaniline,
N-ethyl-N-(3-sulfopropyl)-3,5-dimethylaniline,
N-ethyl-N-(2-hydroxy-3-sulfopropyl)-3-methoxyaniline,
N-ethyl-N-(2-hydroxy-3-sulfopropyl)aniline, N-ethyl-N-(3-methylphenyl)-N'-succinylethylene diamine (EMSE),
N-ethyl-N-(3-methylphenyl)-N'-acetylethylene diamine, and
N-ethyl-N-(2-hydroxy-3-sulfopropyl)-4-fluoro-3,5-dimethoxyaniline (F-DAOS).

When a peroxidative substance such as peroxidase, and one part of oxidative coupling type chromogens are used as a reagent for removing hydrogen peroxide, concentration of the one part of oxidative coupling type chromogens is not specifically limited as long as removal of the generated hydrogen peroxide can be performed, and the concentration is preferably 0.05 to 4 g/L, and more preferably 0.1 to 2 g/L.

When catalase is used as a reagent for removing hydrogen peroxide in step (ii) of the present invention, it is preferred that a catalase inhibitor is co-present in step (iv). Examples of catalase inhibitors include sodium azide, $H_2S$, HCN, $NH_2OH$, 3-amino-1,2,4-triazole. Concentration thereof is not specifically limited as long as catalase activity can be inhibited and the measurement of the generated hydrogen peroxide in step (iv) can not be affected, and the concentration is preferably 0.5 to 60 mmol/L, and more preferably 1 to 30 mmol/L.

A method for measuring the generated hydrogen peroxide derived from triglycerides in LDL in step (iv) of the present invention includes a method for measuring directly with a hydrogen peroxide electrode, a method for measuring with a reagent for measuring hydrogen peroxide. A reagent for measuring hydrogen peroxide is a reagent for converting the generated hydrogen peroxide into a detectable substance. Detectable substances include a dye and a luminescent substance, and a dye is preferred. When the detectable substance is a dye, the reagent for measuring hydrogen peroxide comprises oxidative coloring-type chromogens, and a peroxidative substance such as peroxidase. Oxidative coloring-type chromogens include the above-mentioned oxidative coupling-type chromogens, and the leuco-type chromogens described in the following. When the detectable substance is a luminescent substance, the reagent for measuring hydrogen peroxide comprises a luminescent substance. A luminescent substance includes luminol, isoluminol, lucigenin, and acryl-dinium ester.

When a reagent comprising oxidative coloring-type chromogens and a peroxidative substance such as peroxidase are used as a reagent for measuring hydrogen peroxide, hydrogen peroxide can be measured by reacting the hydrogen peroxide with oxidative coloring-type chromogens in the presence of a peroxidative substance to generate a dye, and measuring the generated dye. Further, when a reagent for measuring hydrogen peroxide comprising a luminescent substance is used, hydrogen peroxide can be measured by reacting the hydrogen peroxide with a luminescent substance, and measuring the generated light photon.

An oxidative coupling-type chromogen is a chromogen that reacts with hydrogen peroxide in the presence of a peroxidative substance such as peroxidase and gives a dye by an oxidative-coupling reaction. As mentioned above, an oxidative-coupling reaction of a coupler such as 4-AA with a phenol-type hydrogen donor or an aniline-hydrogen donor generates a dye.

A leuco-type chromogen is a chromogen that generates a dye only by itself, by reacting with hydrogen peroxide in the presence of a peroxidative substance such as peroxidase. Specific examples include:
10-N-carboxymethylcarbamoyl-3,7-bis(dimethylamino)-10H-phenothiazine (CCAP),
10-N-methylcarbamoyl-3,7-bis(dimethylamino)-10H-phenothiazine (MCDP),
N-(carboxymethylaminocarbonyl)-4,4'-bis(dimethylamino) diphenylamine sodium salt (DA-64),
4,4'-bis(dimethylamino)diphenylamine, and
bis[3-bis(4-chlorophenyl)methyl-4-dimethylaminophenyl] amine (BCMA).

When a peroxidative substance such as peroxidase and one part of oxidative coupling-type chromogens are used as the reagent for removing hydrogen peroxide in step (ii), and oxidative coupling-type chromogens and a peroxidative substance such as peroxidase are used as the reagent for measuring hydrogen peroxide in step (iv), the other part of oxidative coupling-type chromogens used in step (ii) can be used as the reagent for measuring hydrogen peroxide in step (iv). In other words, when a coupler such as 4-AA is used as a oxidative coupling-type chromogen in the step of removing hydrogen peroxide in step (ii), a phenol-type hydrogen donor or an aniline-type hydrogen donor are to be added in step (iv), and when a phenol-type hydrogen donor or an aniline-type hydrogen donor are used in the step of removing hydrogen peroxide, a coupler such as 4-AA is to be added in step (iv).

For measuring hydrogen peroxide, concentration of a peroxidative substance is not specifically limited as long as measurement can be performed. When peroxidase is used as a peroxidative substance, the concentration is preferably 1 to 100 U/mL and more preferably 2 to 50 U/mL. Concentration of an oxidative coloring-type chromogen is not specifically limited as long as measurement can be performed, and the concentration is preferably 0.01 to 10 g/L, and more preferably 0.02 to 5 g/L.

The combinations of the step of removing free glycerol present in the reaction solution in step (ii) and the method for measuring free glycerol in step (iv) of the present invention are not limited to the above-mentioned examples.

For example, a method which comprises converting the free glycerol into glycerol-3-phosphate by glycerol kinase in step (ii) and measuring the hydrogen peroxide generated by the action of glycerol oxidase in the presence of an activating agent of glycerol kinase or the like in step (iv) can be exemplified.

A kit for measuring triglycerides in LDL of the present invention is preferably composed of two reagents of the following first reagent and second reagent, and it may be suitably composed of three reagents, or the like.

First Reagent:
a reagent comprising at least one surfactant selected from the group consisting of POE-POA polycyclic phenyl ether, POP-POA polycyclic phenyl ether, POE alkylphenyl ether formaldehyde condensate, and POE polycyclic phenyl ether having a HLB value of 13.0 or higher and 17.0 or lower; lipoprotein lipase; and a reagent for removing free glycerol.

Second Reagent:
a reagent comprising at least one surfactant selected from the group consisting of POE-POA alkyl ether, POP-POA alkyl ether, POE-POA alkylphenyl ether, POP-POA alkylphenyl ether, POE polycyclic phenyl ether condensate, POE alkylphenyl ether alkylphenyl sulfate, POE polycyclic phenyl ether sulfate, and POE polycyclic phenyl ether having a HLB value of 9.0 or higher and lower than 13.0; and a reagent for measuring free glycerol.

Lipoprotein lipase, surfactant, a reagent for removing free glycerol, and a reagent for measuring free glycerol used in the kit for measuring triglycerides in LDL of the present invention can be exemplified by the aforementioned ones.

In the kit for measuring triglycerides in LDL composed of two reagents of a first reagent and second reagent, enzymes that generate hydrogen peroxide from triglyceride are contained in the first reagent, and can be further contained in the second reagent.

A reagent for removing hydrogen peroxide is contained in the first reagent. When catalase is used as a reagent for removing hydrogen peroxide, it is preferred that the second reagent comprises a catalase activity-inhibitor. The catalase activity-inhibitor can be exemplified by the above-mentioned catalase activity-inhibitors. When a reagent comprising a peroxidative substance such as peroxidase and one part of oxidative coupling-type chromogens is used as a reagent for removing hydrogen peroxide, it is not necessary to remove or inactivate the reagent for removing hydrogen peroxide because the peroxidative substance and the one part of oxidative coupling-type chromogens are also components of a reagent for measuring hydrogen peroxide, and it is sufficient to add the other part of oxidative coupling-type chromogens necessary for coloring to the second reagent. Moreover, when catalase is used as a reagent for removing hydrogen peroxide-removing reagent, a part of components of a reagent for measuring hydrogen peroxide, particularly one part of oxidative coupling-type chromogens may be contained in the first reagent. A bile acid derivative may be contained in either one of, or both of a first reagent and a second reagent, and is preferably contained in the second reagent.

The kit for measuring triglycerides in LDL of the present invention may comprise, according to need, a reaction solution, a stabilizer, an antiseptic, an interference inhibitor, a reaction promoter, an inhibitor of non-specific reaction, etc. Examples of the reaction solution include the above-mentioned reaction solution. Examples of the stabilizer include ethylenediaminetetraacetic acid (EDTA), sucrose, calcium chloride, amino acids, albumin, etc. Examples of the antiseptic include sodium azide and antibiotics. Examples of the interference inhibitor include ascorbate oxidase for eliminating influence of ascorbic acid. Examples of the reaction promoter include enzymes such as colipase and phospholipase, salts such as sodium sulfate, sodium chloride, and magnesium sulfate, etc. Examples of the inhibitor of non-specific reaction include macromolecular substance such as dextran sulfate.

A kit for measuring triglycerides in LDL of the present invention may be in a state of being lyophilized or being dissolved in a reaction solution. When triglycerides in LDL in a sample are measured using the kit in a state of being lyophilized, the kit may be used after being dissolved in the above-mentioned aqueous medium or reaction solution.

Lipoprotein lipase in a kit for measuring triglycerides in LDL of the present invention is contained in such amount that the concentration thereof in the state of being dissolved in an aqueous medium becomes preferably 0.01 to 1200 U/mL, and more preferably 0.02 to 600 U/mL. Glycerol kinase in a kit for measuring triglycerides in LDL of the present invention is contained in such amount that the concentration thereof in the state of being dissolved in an aqueous medium becomes preferably 0.1 to 60 U/mL, and more preferably 0.2 to 30 U/mL. Glycerol-3-phosphate oxidase in a kit for measuring triglycerides in LDL of the present invention is contained in such amount that the concentration thereof in the state of being dissolved in an aqueous medium becomes preferably 1 to 180 U/mL, and more preferably 2 to 90 U/mL.

Surfactant in a kit for measuring triglycerides in LDL of the present invention is contained in such amount that the concentration thereof in the state of being dissolved in an aqueous medium becomes preferably 0.01 to 20%, and more preferably 0.02 to 10%.

Catalase in a kit for measuring triglycerides in LDL using catalase as a reagent for removing hydrogen peroxide is contained in such amount that the concentration thereof in the state of being dissolved in an aqueous medium becomes preferably 0.05 to 1.2 kU/mL, and more preferably 0.1 to 6.0 kU/mL. Catalase activity-inhibitor in a kit for measuring triglycerides in LDL using catalase as a reagent for removing hydrogen peroxide is contained in such amount that the concentration thereof in the state of being dissolved in an aqueous medium becomes preferably 0.5 to 180 mmol/L, and more preferably 1 to 90 mmol/L.

Peroxidase and one part of oxidative coupling-type chromogens in a kit for measuring triglycerides in LDL using a peroxidative substance such as peroxidase and one part of oxidative coupling-type chromogens as a reagent for removing hydrogen peroxide are contained in such amount that the concentration thereof in the state of being dissolved in an aqueous medium become preferably 1 to 600 U/mL and 0.05 to 8 g/L, respectively, and more preferably 2 to 150 U/mL and 0.1 to 4 g/L, respectively.

Peroxidase and oxidative coupling-type chromogens in a kit for measuring triglycerides in LDL using a reagent comprising peroxidase and oxidative coupling-type chromogens as a reagent for measuring hydrogen peroxide are contained in such amount that the concentration thereof in the state of being dissolved in an aqueous medium become preferably 1 to 600 U/mL and 0.05 to 8 g/L, respectively, and more preferably 2 to 150 U/mL and 0.1 to 4 g/L, respectively.

Bile acid derivative in a kit for measuring triglycerides in LDL of the present invention is contained in such amount that the concentration thereof in the state of being dissolved in an aqueous medium becomes preferably 0.01 to 20%, and more preferably 0.02 to 10%.

Certain specific embodiments of the present invention are explained in detail in the following Examples, which are not to be construed as limiting the present invention. In the Examples, reagents and enzymes of the following manufacturers were used.

PIPES (Dojindo Laboratories); MES (Dojindo Laboratories); EMSE (Daito Chemix Corporation); 4-aminoantipyrine (Saikyo Kasei), CEBP-M (enzyme having an activity of lipoprotein lipase; Asahi Kasei Corporation); GYK-301 (glycerol kinase; Toyobo Co., Ltd.); GPOM (glycerol 3-phosphate oxidase; Asahi Kasei Corporation), catalase (Sigma), peroxidase (Toyobo Co., Ltd.), sodium azide (Kanto Chemicals Co., Inc.), Emulgen B66 (Kao Corporation), Newcol 610 (Nippon Nyukazai Co., Ltd.), Newcol 2608F (Nippon Nyukazai Co., Ltd.), New Calgen GP120 (Takemoto Oil & Fat, Co. Ltd.), NIKKOL R1020 (Nikko Chemicals Co., Ltd.), Emulgen A60 (Kao Corporation), BLAUNON DSP12.5 (Aoki Oil Industrial Co., Ltd.), HI-TENOL N08 (Daichi Kogyo Co., Ltd.), Emulgen L40 (Kao Corporation), Newcol 707SF (Nippon Nyukazai Co., Ltd.), Wondersurf S1400 (Aoki Oil Industrial Co., Ltd.), New Calgen E150 (Takemoto Oil & Fat, Co. Ltd.), Sodium cholate (Acros), Emulgen 909 (POE nonylphenyl ether HLB 12.4; Kao Corporation), Emulmin NL70 (POE lauryl ether HLB 12.4; Sanyo Chemicals Industries, Ltd.).

EXAMPLE 1

A kit for measuring triglyceride in LDL consisting of the following first reagent (reagent A) and second reagent (reagent a) was prepared.

First Reagent (Reagent A)

| | |
|---|---|
| PIPES (pH 7.0) | 20 mmol/L |
| EMSE | 0.3 g/L |
| Magnesium sulfate | 0.5 g/L |
| Emulgen B66 | 5 g/L |
| CEBP-M | 2 kU/L |
| GYK-301 | 2 kU/L |
| GPOM | 10 kU/L |
| catalase | 200 kU/L |

Second Reagent (Reagent a)

| | |
|---|---|
| PIPES (pH 7.0) | 20 mmol/L |
| 4-aminoantipyrine | 0.3 g/L |
| peroxidase | 20 kU/L |
| sodium azide | 0.5 g/L |
| Emulgen A60 | 20 g/L |

EXAMPLE 2

A kit for measuring triglyceride in LDL consisting of the following first reagent (reagent B) and second reagent (reagent a) was prepared.

First Reagent (Reagent B)

| | |
|---|---|
| PIPES (pH 7.0) | 20 mmol/L |
| EMSE | 0.3 g/L |
| Magnesium sulfate | 0.5 g/L |
| Newcol 610 | 5 g/L |
| CEBP-M | 2 kU/L |
| GYK-301 | 2 kU/L |
| GPOM | 10 kU/L |
| catalase | 200 kU/L |

Second Reagent (Reagent a)

| | |
|---|---|
| PIPES (pH 7.0) | 20 mmol/L |
| 4-aminoantipyrine | 0.3 g/L |
| peroxidase | 20 kU/L |
| sodium azide | 0.5 g/L |
| Emulgen A60 | 20 g/L |

EXAMPLE 3

A kit for measuring triglyceride in LDL consisting of the following first reagent (reagent C) and second reagent (reagent a) was prepared.

First Reagent (Reagent C)

| | |
|---|---|
| PIPES (pH 7.0) | 20 mmol/L |
| EMSE | 0.3 g/L |
| Magnesium sulfate | 0.5 g/L |
| Newcol 2608F | 5 g/L |
| CEBP-M | 2 kU/L |
| GYK-301 | 2 kU/L |
| GPOM | 10 kU/L |
| catalase | 200 kU/L |

Second Reagent (Reagent a)

| | |
|---|---|
| PIPES (pH 7.0) | 20 mmol/L |
| 4-aminoantipyrine | 0.3 g/L |
| peroxidase | 20 kU/L |
| sodium azide | 0.5 g/L |
| Emulgen A60 | 20 g/L |

EXAMPLE 4

A kit for measuring triglyceride in LDL consisting of the following first reagent (reagent D) and second reagent (reagent a) was prepared.

First Reagent (Reagent D)

| | |
|---|---|
| PIPES (pH 7.0) | 20 mmol/L |
| EMSE | 0.3 g/L |
| Magnesium sulfate | 0.5 g/L |
| Newcol 1020 | 2 g/L |
| CEBP-M | 2 kU/L |
| GYK-301 | 2 kU/L |
| GPOM | 10 kU/L |
| catalase | 200 kU/L |

Second Reagent (Reagent a)

| | |
|---|---|
| PIPES (pH 7.0) | 20 mmol/L |
| 4-aminoantipyrine | 0.3 g/L |
| peroxidase | 20 kU/L |
| sodium azide | 0.5 g/L |
| Emulgen A60 | 20 g/L |

EXAMPLE 5

A kit for measuring triglyceride in LDL consisting of the following first reagent (reagent E) and second reagent (reagent a) was prepared.

First Reagent (Reagent E)

| | |
|---|---|
| PIPES (pH 7.0) | 20 mmol/L |
| EMSE | 0.3 g/L |
| Magnesium sulfate | 0.5 g/L |
| New Calgen GP120 | 5 g/L |
| CEBP-M | 2 kU/L |
| GYK-301 | 2 kU/L |
| GPOM | 10 kU/L |
| catalase | 200 kU/L |

Second Reagent (Reagent a)

| | |
|---|---|
| PIPES (pH 7.0) | 20 mmol/L |
| 4-aminoantipyrine | 0.3 g/L |
| peroxidase | 20 kU/L |
| sodium azide | 0.5 g/L |
| Emulgen A60 | 20 g/L |

EXAMPLE 6

A kit for measuring triglyceride in LDL consisting of the following first reagent (reagent A) and second reagent (reagent b) was prepared.

First Reagent (Reagent A)

| | |
|---|---|
| PIPES (pH 7.0) | 20 mmol/L |
| EMSE | 0.3 g/L |
| Magnesium sulfate | 0.5 g/L |
| Emulgen B66 | 5 g/L |
| CEBP-M | 2 kU/L |
| GYK-301 | 2 kU/L |
| GPOM | 10 kU/L |
| catalase | 200 kU/L |

Second Reagent (Reagent b)

| | |
|---|---|
| PIPES (pH 7.0) | 20 mmol/L |
| 4-aminoantipyrine | 0.3 g/L |
| peroxidase | 20 kU/L |
| sodium azide | 0.5 g/L |
| BLAUNON DSP12.5 | 10 g/L |

EXAMPLE 7

A kit for measuring triglyceride in LDL consisting of the following first reagent (reagent A) and second reagent (reagent c) was prepared.

First Reagent (Reagent A)

| | |
|---|---|
| PIPES (pH 7.0) | 20 mmol/L |
| EMSE | 0.3 g/L |
| Magnesium sulfate | 0.5 g/L |
| Emulgen B66 | 5 g/L |
| CEBP-M | 2 kU/L |
| GYK-301 | 2 kU/L |
| GPOM | 10 kU/L |
| catalase | 200 kU/L |

Second Reagent (Reagent c)

| | |
|---|---|
| PIPES (pH 7.0) | 20 mmol/L |
| 4-aminoantipyrine | 0.3 g/L |
| peroxidase | 20 kU/L |
| sodium azide | 0.5 g/L |
| Emulgen L40 | 5 g/L |

EXAMPLE 8

A kit for measuring triglyceride in LDL consisting of the following first reagent (reagent A) and second reagent (reagent d) was prepared.

First Reagent (Reagent A)

| | |
|---|---|
| PIPES (pH 7.0) | 20 mmol/L |
| EMSE | 0.3 g/L |
| Magnesium sulfate | 0.5 g/L |
| Emulgen B66 | 5 g/L |
| CEBP-M | 2 kU/L |
| GYK-301 | 2 kU/L |
| GPOM | 10 kU/L |
| catalase | 200 kU/L |

Second Reagent (Reagent d)

| | |
|---|---|
| PIPES (pH 7.0) | 20 mmol/L |
| 4-aminoantipyrine | 0.3 g/L |
| peroxidase | 20 kU/L |
| sodium azide | 0.5 g/L |
| HI-TENOL N08 | 6 g/L |

EXAMPLE 9

A kit for measuring triglyceride in LDL consisting of the following first reagent (reagent A) and second reagent (reagent e) was prepared.

First Reagent (Reagent A)

| | |
|---|---|
| PIPES(pH 7.0) | 20 mmol/L |
| EMSE | 0.3 g/L |
| Magnesium sulfate | 0.5 g/L |
| Emulgen B66 | 5 g/L |
| CEBP-M | 2 kU/L |
| GYK-301 | 2 kU/L |
| GPOM | 10 kU/L |
| catalase | 200 kU/L |

Second Reagent (Reagent e)

| | |
|---|---|
| PIPES(pH 7.0) | 20 mmol/L |
| 4-aminoantipyrine | 0.3 g/L |
| peroxidase | 20 kU/L |
| sodium azide | 0.5 g/L |
| Newcol 707SF | 5 g/L |

EXAMPLE 10

A kit for measuring triglyceride in LDL consisting of the following first reagent (reagent A) and second reagent (reagent f) was prepared.

First Reagent (Reagent A)

| | |
|---|---|
| PIPES(pH 7.0) | 20 mmol/L |
| EMSE | 0.3 g/L |
| Magnesium sulfate | 0.5 g/L |
| Emulgen B66 | 5 g/L |
| CEBP-M | 2 kU/L |
| GYK-301 | 2 kU/L |
| GPOM | 10 kU/L |
| catalase | 200 kU/L |

Second Reagent (Reagent f)

| | |
|---|---|
| PIPES(pH 7.0) | 20 mmol/L |
| 4-aminoantipyrine | 0.3 g/L |
| peroxidase | 20 kU/L |
| sodium azide | 0.5 g/L |
| Wondersurf S1400 | 6 g/L |

EXAMPLE 11

A kit for measuring triglyceride in LDL consisting of the following first reagent (reagent A) and second reagent (reagent g) was prepared.

First Reagent (Reagent A)

| | |
|---|---|
| PIPES(pH 7.0) | 20 mmol/L |
| EMSE | 0.3 g/L |
| Magnesium sulfate | 0.5 g/L |
| Emulgen B66 | 5 g/L |
| CEBP-M | 2 kU/L |
| GYK-301 | 2 kU/L |
| GPOM | 10 kU/L |
| catalase | 200 kU/L |

Second Reagent (Reagent g)

| | |
|---|---|
| PIPES(pH 7.0) | 20 mmol/L |
| 4-aminoantipyrine | 0.3 g/L |
| peroxidase | 20 kU/L |
| sodium azide | 0.5 g/L |
| New Calgen E150 | 6 g/L |

COMPARATIVE EXAMPLE 1

A kit for measuring triglyceride in LDL consisting of the following first reagent (reagent F) and second reagent (reagent a) was prepared.

First Reagent (Reagent F)

| | |
|---|---|
| PIPES(pH 7.0) | 20 mmol/L |
| EMSE | 0.3 g/L |
| Magnesium sulfate | 0.5 g/L |
| CEBP-M | 2 kU/L |
| GYK-301 | 2 kU/L |
| GPOM | 10 kU/L |
| catalase | 200 kU/L |

Second Reagent (Reagent a)

| | |
|---|---|
| PIPES(pH 7.0) | 20 mmol/L |
| 4-aminoantipyrine | 0.3 g/L |
| peroxidase | 20 kU/L |
| sodium azide | 0.5 g/L |
| Emulgen A60 | 20 g/L |

COMPARATIVE EXAMPLE 2

A kit for measuring triglyceride in LDL consisting of the following first reagent (reagent A) and second reagent (reagent h) was prepared.

First Reagent (Reagent A)

| | |
|---|---|
| PIPES(pH 7.0) | 20 mmol/L |
| EMSE | 0.3 g/L |
| Magnesium sulfate | 0.5 g/L |
| Emulgen B66 | 5 g/L |
| CEBP-M | 2 kU/L |
| GYK-301 | 2 kU/L |
| GPOM | 10 kU/L |
| catalase | 200 kU/L |

Second Reagent (Reagent h)

| | |
|---|---|
| PIPES(pH 7.0) | 20 mmol/L |
| 4-aminoantipyrine | 0.3 g/L |
| peroxidase | 20 kU/L |
| sodium azide | 0.5 g/L |

COMPARATIVE EXAMPLE 3

A kit for measuring triglyceride in LDL consisting of the following first reagent (reagent A) and second reagent (reagent i) was prepared.

First Reagent (Reagent A)

| | |
|---|---|
| PIPES(pH 7.0) | 20 mmol/L |
| EMSE | 0.3 g/L |
| Magnesium sulfate | 0.5 g/L |

-continued

| | |
|---|---|
| Emulgen B66 | 5 g/L |
| CEBP-M | 2 kU/L |
| GYK-301 | 2 kU/L |
| GPOM | 10 kU/L |
| catalase | 200 kU/L |

Second Reagent (Reagent i)

| | |
|---|---|
| PIPES(pH 7.0) | 20 mmol/L |
| 4-aminoantipyrine | 0.3 g/L |
| peroxidase | 20 kU/L |
| sodium azide | 0.5 g/L |
| Emulgen 909 | 10 g/L |

COMPARATIVE EXAMPLE 4

A kit for measuring triglyceride in LDL consisting of the following first reagent (reagent A) and second reagent (reagent j) was prepared.

First Reagent (Reagent A)

| | |
|---|---|
| PIPES(pH 7.0) | 20 mmol/L |
| EMSE | 0.3 g/L |
| Magnesium sulfate | 0.5 g/L |
| Emulgen B66 | 5 g/L |
| CEBP-M | 2 kU/L |
| GYK-301 | 2 kU/L |
| GPOM | 10 kU/L |
| catalase | 200 kU/L |

Second Reagent (Reagent j)

| | |
|---|---|
| PIPES(pH 7.0) | 20 mmol/L |
| 4-aminoantipyrine | 0.3 g/L |
| peroxidase | 20 kU/L |
| sodium azide | 0.5 g/L |
| Emulmin NL70 | 6 g/L |

EXAMPLE 12

According to the ultracentrifugation method described in "New Chemical Experiment course 4" (Tokyo Kagaku Dojin), five lipoprotein fractions of HDL (specific gravity>1.063), LDL in a narrow sense (specific gravity 1.019-1.063), IDL (specific gravity 1.006 to 1.019), VLDL (specific gravity 0.96 to 1.006) and CM (specific gravity<0.96) were collected respectively from human sera, and the reactivity of triglycerides for each lipoprotein fraction was calculated by using the kits of Examples 1 to 11, and Comparative Examples 1 to 4.

(1) Calculation of the "Reaction Absorbance" in Each Lipoprotein Fraction, from the Reaction of Triglyceride in Each Lipoprotein Fraction with the Kits of Examples 1 to 11 and Comparative Examples 1 to 4

The "reaction absorbance" was calculated by the following operation by using HITACHI 7170S Autoanalyzer.

Each lipoprotein fraction was used as a sample, and added into a reaction cell (2 μL). Then, the first reagent (0.15 mL) of each of the kits of Examples 1 to 11 and Comparative Examples 1 and 2 was added to start the reaction (first reaction). Each mixture was incubated at 37° C. for 5 min, and the absorbance (E1) of the reaction solution 5 min after the reaction was calculated at a main wavelength of 600 nm and sub-wavelength of 700 nm. Then, the second reagent (0.05 mL) of each of the kits of Examples 1 to 11 and Comparative Examples 1 to 4 was added separately to the reaction solution, and the mixture was incubated at 37° C. for 5 min to carry out the reaction (second reaction), and the absorbance (E2) of the reaction solution 5 min after the second reaction was measured at a main wavelength of 600 nm and sub-wavelength of 700 nm. E1 was subtracted from E2 to calculate the absorbance change ($\Delta E_{lipoprotein\ fraction}$). Further, saline solution was used instead of each lipoprotein fraction as a sample, and the similar measurements were performed to calculate the absorbance change ($\Delta E_{blank}$). Finally, the "reaction absorbance" in each lipoprotein fraction was calculated using the following formula.

$$\text{Reaction absorbance in lipoprotein fraction} = \Delta E_{lipoprotein\ fraction} - E_{blank} \qquad \text{(formula 1)}$$

(2) Calculation of Reactivity of Triglyderides in Each Lipoprotein Fraction

By using HITACHI 7170S Autoanalyzer, the "reaction absorbance" was calculated by a method similar to (1), except using DETERMINER C TG (Kyowa Medex Co., Ltd.) which is a kit for measuring triglycerides comprising EMSE as a chromogen instead of the kit of Example 1. The reaction ratio (%) of triglycerides in each lipoprotein fraction of the kits of Examples 1 to 11 and Comparative Examples 1 to 4 was calculated using the following formula. The "reaction absorbance" calculated in the measurement using DETERMINER C TG means a "reaction absorbance" observed when all of triglycerides in the targeted lipoprotein was reacted.

$$\text{Reactivity (\%)} = \frac{\text{Reaction absorbance with the kit of Ex. 1}}{\text{Reaction absorbance with DETAMINER C CTG}} \times 100$$

For the reactivity of triglyceride in each lipoprotein fraction in the kits of Examples 1 to 11 and Comparative Examples 1 to 4, when the reactivity is 0 to 10%, it is denoted as "−", when 10 to 20% as "±", when 20 to 40% as "+", when 40 to 60% as "++", when 60 to 80% as "+++", and when 80 to 100% as "++++". The results are shown in Table 1.

TABLE 1

| Kit | HDL | LDL | IDL | VLDL | CM |
|---|---|---|---|---|---|
| Example 1 | − | ++ | + | − | − |
| Example 2 | − | ++ | + | − | − |
| Example 3 | − | ++ | − | − | − |
| Example 4 | − | ++ | + | − | − |
| Example 5 | − | +++ | + | − | − |
| Example 6 | − | ++ | − | − | − |
| Example 7 | − | ++ | + | − | − |
| Example 8 | − | + | − | − | − |
| Example 9 | − | + | − | − | − |
| Example 10 | − | ++ | + | − | − |
| Example 11 | − | + | − | − | − |
| Comparative Example 1 | ++++ | +++ | + | − | − |
| Comparative Example 2 | − | − | − | − | − |
| Comparative Example 3 | − | +++ | ++ | ++ | + |
| Comparative Example 4 | − | ++ | ++ | + | + |

It was revealed that triglycerides in LDL react preferentially only using a kit comprising one surfactant selected from the group consisting of POE-POA polycyclic phenyl ether, POE alkylphenyl ether formaldehyde condensate, and POE polycyclic phenyl ether having a HLB value of 13.0 or higher and 17.0 or lower in the first reagent; and one surfactant selected from the group consisting of POE-POA alkyl ether, POE-POA alkylphenyl ether, POE polycyclic phenyl ether condensate, POE alkylphenyl ether sulfate, POE polycyclic phenyl ether sulfate and POE polycyclic phenyl ether having a HLB value of 9.0 or higher and lower than 13.0 in the second reagent.

EXAMPLE 13

A kit for measuring triglyceride in LDL consisting of the following first reagent (reagent A) and second reagent (reagent k) was prepared.
First Reagent (Reagent A)

| | |
|---|---|
| PIPES(pH 7.0) | 20 mmol/L |
| EMSE | 0.3 g/L |
| Magnesium sulfate | 0.5 g/L |
| Emulgen B66 | 5 g/L |
| CEBP-M | 2 kU/L |
| GYK-301 | 2 kU/L |
| GPOM | 10 kU/L |
| catalase | 200 kU/L |

Second Reagent (Reagent k)

| | |
|---|---|
| PIPES(pH 7.0) | 20 mmol/L |
| 4-aminoantipyrine | 0.3 g/L |
| peroxidase | 20 kU/L |
| sodium azide | 0.5 g/L |
| Emulgen A60 | 20 g/L |
| Sodium cholate | 6 g/L |

EXAMPLE 14

A kit for measuring triglyceride in LDL consisting of the following first reagent (reagent A) and second reagent (reagent l) was prepared.
First Reagent (Reagent A)

| | |
|---|---|
| PIPES(pH 7.0) | 20 mmol/L |
| EMSE | 0.3 g/L |
| Magnesium sulfate | 0.5 g/L |
| Emulgen B66 | 5 g/L |
| CEBP-M | 2 kU/L |
| GYK-301 | 2 kU/L |
| GPOM | 10 kU/L |
| catalase | 200 kU/L |

Second Reagent (Reagent l)

| | |
|---|---|
| PIPES(pH 7.0) | 20 mmol/L |
| 4-aminoantipyrine | 0.3 g/L |
| peroxidase | 20 kU/L |
| sodium azide | 0.5 g/L |
| HI-TENOL N08 | 6 g/L |
| Sodium cholate | 6 g/L |

EXAMPLE 15

A kit for measuring triglyceride in LDL consisting of the following first reagent (reagent A) and second reagent (reagent m) was prepared.
First Reagent (Reagent A)

| | |
|---|---|
| PIPES(pH 7.0) | 20 mmol/L |
| EMSE | 0.3 g/L |
| Magnesium sulfate | 0.5 g/L |
| Emulgen B66 | 5 g/L |
| CEBP-M | 2 kU/L |
| GYK-301 | 2 kU/L |
| GPOM | 10 kU/L |
| catalase | 200 kU/L |

Second Reagent (Reagent m)

| | |
|---|---|
| PIPES(pH 7.0) | 20 mmol/L |
| 4-aminoantipyrine | 0.3 g/L |
| peroxidase | 20 kU/L |
| sodium azide | 0.5 g/L |
| Emulgen A60 | 20 g/L |
| HI-TENOL N08 | 6 g/L |
| Sodium cholate | 6 g/L |

EXAMPLE 16

Using the kits of Example 1, Example 8, Examples 13 to 15 and Comparative Example 2, the reaction absorbance to triglycerides in 30 human serum samples was calculated by using HITACHI 7170S Autoanalyzer by a measuring method similar to the measuring method of Example 12 (1).

Then, using the ultracentrifugation method described in Kidney International, Vol. 39, p. 755 (1991) as a standard method, the 30 serum samples were ultracentrifuged to separate LDL fraction (specific gravity 1.006 to 1.063) for each sample, and the amounts of triglycerides in the obtained LDL fractions were measured by using DETERMINER C TG (Kyowa Medex Co., Ltd.). The correlation coefficients between the measurement using the kits of each Example and Comparative Example and the measurement by the standard method are shown in Table 2.

TABLE 2

| Kit | Surfactant used in the second reagent | correlation coefficient |
|---|---|---|
| Example 1 | Emulgen A60 | 0.821 |
| Example 8 | HI-TENOL N08 | 0.831 |
| Example 13 | Emulgen A60, cholic acid | 0.898 |
| Example 14 | HI-TENOL N08, cholic acid | 0.898 |
| Example 15 | Emulgen A60, cholic acid, HI-TENOL N08 | 0.926 |
| Comparative Example 2 | Not added | 0.714 |

By comparing the measurement using the kit of Example 1 or Example 8 with the measurement using the kit of Comparative Example 2, it was revealed that the correlation coefficient against the standard method increases when a second reagent comprising POE polycyclic phenyl ether having a HLB value of 9.0 or higher and lower than 13.0, or POE alkylphenyl ether sulfate is used. Further, by comparing the measurement using the kits of Example 1 and Example 13, with the measurement using the kits of Example 8 and Example 14, it was revealed that the correlation coefficient against the standard method increases when cholic acid which belongs to a bile acid was added further to a second reagent comprising POE alkyl polycyclic phenyl ether having a HLB value of 9.0 or higher and lower than 13.0 or POE alkylphenyl ether sulfate. Moreover, from the measurement using the kit of Example 15, it was revealed that a good correlation coefficient against the standard method can also be obtained when a second reagent comprising POE polycyclic phenyl ether having a HLB value of 9.0 or higher and lower than 13.0, POE alkylphenyl ether sulfate and bile acid is used.

EXAMPLE 17

Using the ultracentrifugation method and the kit of Example 15 of the present invention, triglycerides in LDL in each of three fresh human serum samples were quantified by the following method.

(1) Quantification of Triglycerides in LDL by Using the Ultracentrifugation Method LDL (specific gravity 1.006 to 1.063) in each of three fresh human serum samples was separated by using the ultracentrifugation method described in Kidney International, Vo. 39, p. 755 (1991), and the amounts of triglyceride in the obtained LDL fractions were measured by using DETERMINER C TG (Kyowa Medex Co., Ltd.).

(2) Preparation of a Calibration Curve

Fresh human serum with the concentration of 40.0 mg/dL of triglycerides in LDL, which was determined by a measurement using an ultracentrifugation method, was used as a standard, and was used as a sample for preparing a calibration curve. According to the measuring method similar to that of Example 12 (1), the reaction absorbance of the sample for preparing a calibration curve was measured on HITACHI 7170S Autoanalyzer, and a calibration curve was prepared based on the relationship of the reaction absorbance and the concentration of triglycerides in LDL in the sample for preparing a calibration curve.

(3) Quantification of Triglycerides in LDL of 3 Human Serum Samples

Using three samples of fresh human sera instead of the samples for preparing a calibration curve, the concentrations of triglycerides in LDL of each of the samples were determined according to the method similar to that of the above (2), which comprises carrying out the reaction for each of the two samples, and correlating the absorbances of the reaction solution after the reaction with the calibration curve prepared in the above (2).

The measurements by the ultracentrifugation method in the above (1) and the measurements using the kit of Example 15 for the three samples are shown in Table 3.

TABLE 3

| | LDL-TG concentration (mg/dL) | |
|---|---|---|
| | Ultracentrifugation method | Example 15 |
| Serum 1 | 20.2 | 18.6 |
| Serum 2 | 29.8 | 28.2 |
| Serum 3 | 56.1 | 54.7 |

REFERENCE EXAMPLE 1

The following measuring kits A and B consisting of the following first reagent and second reagent were prepared.

Measuring Kit A
First Reagent

| | |
|---|---|
| PIPES(pH 7.0) | 20 mmol/L |
| EMSE | 0.3 g/L |
| Magnesium sulfate | 0.5 g/L |
| CEBP-M | 2 kU/L |
| GY-301 | 2 kU/L |
| GPOM | 10 kU/L |
| Emulgen B66 | 5 g/L |

Second Reagent

| | |
|---|---|
| PIPES(pH 7.0) | 20 mmol/L |
| 4-aminoantipyrine | 0.3 g/L |
| peroxidase | 20 kU/L |

Measuring Kit B
First Reagent

| | |
|---|---|
| PIPES(pH 7.0) | 20 mmol/L |
| EMSE | 0.3 g/L |
| Magnesium sulfate | 0.5 g/L |
| GY-301 | 2 kU/L |
| GPOM | 10 kU/L |
| Emulgen B66 | 5 g/L |

Second Reagent

| | |
|---|---|
| PIPES(pH 7.0) | 20 mmol/L |
| 4-aminoantipyrine | 0.3 g/L |
| peroxidase | 20 kU/L |

REFERENCE EXAMPLE 2

The following measuring kits A and B consisting of the following first reagent and second reagent were prepared.

Measuring Kit A
First Reagent

| | |
|---|---|
| PIPES(pH 7.0) | 20 mmol/L |
| EMSE | 0.3 g/L |
| Magnesium sulfate | 0.5 g/L |
| CEBP-M | 2 kU/L |
| GY-301 | 2 kU/L |
| GPOM | 10 kU/L |
| Newcol 610 | 5 g/L |

Second Reagent

| | |
|---|---|
| PIPES(pH 7.0) | 20 mmol/L |
| 4-aminoantipyrine | 0.3 g/L |
| peroxidase | 20 kU/L |

Measuring Kit B
First Reagent

| | |
|---|---|
| PIPES(pH 7.0) | 20 mmol/L |
| EMSE | 0.3 g/L |
| Magnesium sulfate | 0.5 g/L |
| GY-301 | 2 kU/L |
| GPOM | 10 kU/L |
| Newcol 610 | 5 g/L |

Second Reagent

| | |
|---|---|
| PIPES(pH 7.0) | 20 mmol/L |
| 4-aminoantipyrine | 0.3 g/L |
| peroxidase | 20 kU/L |

REFERENCE EXAMPLE 3

The following measuring kits A and B consisting of the following first reagent and second reagent were prepared.
Measuring Kit A
First Reagent

| | |
|---|---|
| PIPES(pH 7.0) | 20 mmol/L |
| EMSE | 0.3 g/L |
| Magnesium sulfate | 0.5 g/L |
| CEBP-M | 2 kU/L |
| GY-301 | 2 kU/L |
| GPOM | 10 kU/L |
| Newcol 2608F | 5 g/L |

Second Reagent

| | |
|---|---|
| PIPES(pH 7.0) | 20 mmol/L |
| 4-aminoantipyrine | 0.3 g/L |
| peroxidase | 20 kU/L |

Measuring Kit B
First Reagent

| | |
|---|---|
| PIPES(pH 7.0) | 20 mmol/L |
| EMSE | 0.3 g/L |
| Magnesium sulfate | 0.5 g/L |
| GY-301 | 2 kU/L |
| GPOM | 10 kU/L |
| Newcol 2608F | 5 g/L |

Second Reagent

| | |
|---|---|
| PIPES(pH 7.0) | 20 mmol/L |
| 4-aminoantipyrine | 0.3 g/L |
| peroxidase | 20 kU/L |

REFERENCE EXAMPLE 4

The following measuring kits A and B consisting of the following first reagent and second reagent were prepared.
Measuring Kit A
First Reagent

| | |
|---|---|
| PIPES(pH 7.0) | 20 mmol/L |
| EMSE | 0.3 g/L |
| Magnesium sulfate | 0.5 g/L |
| CEBP-M | 2 kU/L |
| GY-301 | 2 kU/L |
| GPOM | 10 kU/L |
| New Calgen GP120 | 5 g/L |

Second Reagent

| | |
|---|---|
| PIPES(pH 7.0) | 20 mmol/L |
| 4-aminoantipyrine | 0.3 g/L |
| peroxidase | 20 kU/L |

Measuring Kit B
First Reagent

| | |
|---|---|
| PIPES(pH 7.0) | 20 mmol/L |
| EMSE | 0.3 g/L |
| Magnesium sulfate | 0.5 g/L |
| GY-301 | 2 kU/L |
| GPOM | 10 kU/L |
| New Calgen GP120 | 5 g/L |

Second Reagent

| | |
|---|---|
| PIPES(pH 7.0) | 20 mmol/L |
| 4-aminoantipyrine | 0.3 g/L |
| peroxidase | 20 kU/L |

REFERENCE EXAMPLE 5

The following measuring kits A and B consisting of the following first reagent and second reagent were prepared.
Measuring Kit A
First Reagent

| | |
|---|---|
| PIPES(pH 7.0) | 20 mmol/L |
| EMSE | 0.3 g/L |
| Magnesium sulfate | 0.5 g/L |
| CEBP-M | 2 kU/L |
| GY-301 | 2 kU/L |
| GPOM | 10 kU/L |
| NIKKOL R1020 | 2 g/L |

Second Reagent

| | |
|---|---|
| PIPES(pH 7.0) | 20 mmol/L |
| 4-aminoantipyrine | 0.3 g/L |
| peroxidase | 20 kU/L |

Measuring Kit B
First Reagent

| | |
|---|---|
| PIPES(pH 7.0) | 20 mmol/L |
| EMSE | 0.3 g/L |
| Magnesium sulfate | 0.5 g/L |
| GY-301 | 2 kU/L |
| GPOM | 10 kU/L |
| NIKKOL R1020 | 2 g/L |

Second Reagent

| | |
|---|---|
| PIPES(pH 7.0) | 20 mmol/L |
| 4-aminoantipyrine | 0.3 g/L |
| peroxidase | 20 kU/L |

REFERENCE EXAMPLE 6

According to the method similar to that of Example 12, five lipoprotein fractions were collected by the ultracentrifugation method, and the reactivity of triglycerides in each lipoprotein fraction was calculated by using each of the measuring kits A and measuring kits B in Reference Examples 1 to 5.

(1) Calculation of the Reaction Absorbance by the Reaction of Triglyceride in Each Lipoprotein Fraction with Each Measuring Kit The reaction absorbances were calculated by the following operations using HITACHI 7170S Autoanalyzer. Each lipoprotein fraction was used as a sample, and added into a reaction cell (2 μL). Then the first reagent (0.15 mL) of each of the measuring kits A or measuring kits B of Reference Examples 1 to 5 was added to start the reaction (first reaction). Each mixture was incubated at 37° C. for 5 min, and the absorbance (E1) of the reaction solution 5 min after the reaction was measured at a main wavelength of 600 nm, and a sub-wavelength of 700 nm.

Then, the second reagent (0.05 mL) of each of the measuring kits A or measuring kits B of Reference Examples 1 to 5 was added separately to the reaction solution, and the mixture was incubated at 37° C. for 5 min to carry out the reaction (second reaction), and the absorbance (E2) of the reaction solution 5 min after the second reaction was measured at a main wavelength of 600 nm, and a sub-wavelength of 700 nm. E1 was subtracted from E2 to calculate the absorbance change ($\Delta E_{lipoprotein\ fraction}$).

Further, saline solution was used as a sample instead of each lipoprotein fraction, and the similar measurements were performed to calculate the absorbance change ($\Delta E_{blank}$). Finally, the "reaction absorbance" for each lipoprotein fraction was calculated using the following formula 1.

Reaction absorbance for lipoprotein fraction=$\Delta E_{lipoprotein\ fraction} - \Delta E_{blank}$  (formula 1)

Using the reaction absorbances for lipoprotein fractions, obtained on formula 1, in the measurements using the measuring kits A and the measuring kits B of Reference Examples 1 to 5, the reaction absorbance for triglycerides in each lipoprotein fraction was calculated using the following formula, by subtracting the reaction of free glycerol present in each lipoprotein fraction of Reference Examples 1 to 5.

Reaction absorbance for triglycerides in each lipoprotein=reaction absorbance on measuring kit $A$−reaction absorbance on measuring kit $B$ (2) Calculation of Reactivity of Triglycerides in Each Lipoprotein Fraction According to the method similar to that of Example 12, the reaction absorbances observed when triglycerides in the lipoprotein react completely were measured using DETERMINER C TG (Kyowa Medex Co., Ltd.), and the reactivity (%) of triglycerides in each lipoprotein fraction in Reference Examples 1 to 5 was calculated using the following formula.

$$\text{Reactivity (\%)} = \frac{\text{Reaction absorbance with the kit of Reference Examples 1 to 5}}{\text{Reaction absorbance with DETERMINER C TG}} \times 100$$

The reactivity of triglycerides in each lipoprotein fraction in Reference Examples 1 to 5 are shown in Table 3. When the reactivity is 0 to 10% it is denoted as "−", when 10 to 20% as "±", when 20 to 40% as "+", when 40 to 60% as "++", when 60 to 80% as "+++", and when 80 to 100% as "++++".

TABLE 4

| kit | HDL | LDL | IDL | VLDL | CM |
|---|---|---|---|---|---|
| Reference Example 1 | ++++ | ± | ± | − | − |
| Reference Example 2 | +++ | ± | ± | − | − |
| Reference Example 3 | ++++ | + | + | − | − |
| Reference Example 4 | +++ | − | − | − | − |
| Reference Example 5 | +++ | ± | − | − | − |

As shown in Table 4, it was revealed that triglycerides in HDL reacts preferentially in a reagent comprising at least one surfactant selected from the group consisting of polyoxyethylene polyoxyalkylene polycyclic phenyl ether (Newcol 2608F, New Calgen GP120), polyoxyethylene alkylphenyl ether formaldehyde condensate (NIKKOL R1020) and polyoxyethylene polycyclic phenyl ether having a HLB value of 13.0 or higher and 17.0 or lower (Emulgen B66, Newcol 610).

Therefore, triglycerides in lipoproteins other than HDL, specifically LDL, IDL, VLDL, CM remain in a sample treated with a surfactant selected from the group consisting of polyoxyethylene polyoxyalkylene polycyclic phenyl ether, polyoxyethylene alkylphenyl ether formaldehyde condensate and polyoxyethylene polycyclic phenyl ether having a HLB value of 13.0 or higher and 17.0 or lower. Thus, it is possible to measure selectively triglycerides in LDL, by further treating the treated sample with at least one surfactant selected from the group consisting of polyoxyethylene polyoxyalkyene alkyl ether, polyoxypropylene polyoxy alkylene alkyl ether, polyoxyethylene polyoxyalkylene alkylphenyl ether, polyoxypropylene polyoxy alkylene alkylphenyl ether, polyoxyethylene polycyclic phenyl ether condensate, polyoxyethylene alkylphenyl ether sulfate, polyoxyethylene polycyclic phenyl ether sulfate, and polyoxyethylene polycyclic phenyl ether having a HLB value of 9.0 or higher and lower than 13.0.

INDUSTRIAL APPLICABILITY

The present invention provides a method for measuring triglycerides in a low-density lipoprotein and a kit therefor, which are useful for diagnosing coronary artery diseases such as arteriosclerosis.

The invention claimed is:

1. A method for measuring triglycerides in low-density lipoprotein in a sample, wherein the following steps (i) to (v) are performed sequentially:
   (i) a step of generating free glycerol by allowing lipoprotein lipase to act on the sample, in an aqueous medium comprising the sample and at least one surfactant selected from the group consisting of polyoxyethylene polycyclic phenyl ether having a HLB value of 13.0 or higher and 17.0 or lower, polyoxyethylene polyoxyalkelene polycyclic phenyl ether, polyoxypropylene polyoxyalkylene polycyclic phenyl ether and polyoxyethylene alkylphenyl ether formaldehyde condensate;
   (ii) a step of removing free glycerol present in the reaction solution of the above step (i);
   (iii) a step of generating free glycerol by allowing lipoprotein lipase to act on the reaction solution from which free glycerol has been removed in the above step (ii), in the presence of at least one surfactant selected from the group consisting of polyoxyethylene polycyclic phenyl ether having a HLB value of 9.0 or higher and lower than 13.0, polyoxyethylene polyoxyalkylene alkyl ether having a polyoxyalkylene moiety other than polyoxyethylene, polyoxypropylene polyoxyalkylene alkyl ether having a polyoxyalkylene moiety other than polyoxypropylene, polyoxypropylene polyoxyalkylene alkylphenyl ether, polyoxyethylene polycyclic phenyl ether condensate, polyoxyethylene alkylphenyl ether sulfate and polyoxyethylene polycyclic phenyl ether sulfate;

(iv) a step of measuring free glycerol generated in the above step (iii); and (v) a step of correlating the measured free glycerol from step (iv) to an amount of triglycerides in low-density lipoprotein.

2. The method according to claim 1, wherein the free glycerol generated in step (i) is generated from triglycerides in high-density lipoprotein.

3. The method according to claim 1 or 2, wherein the removal of free glycerol in step (ii) is performed by generating hydrogen peroxide with a reagent for generating hydrogen peroxide from free glycerol, and then by removing the hydrogen peroxide.

4. The method according to claim 3, wherein the removal of hydrogen peroxide is performed by allowing catalase to act on the hydrogen peroxide, or allowing a peroxidative substance to act on the hydrogen peroxide in the presence of one part of oxidative coupling chromogen.

5. The method according to claim 4, wherein the measurement of free glycerol in step (iv) is performed by generating hydrogen peroxide with a reagent for generating hydrogen peroxide from free glycerol, and then measuring the hydrogen peroxide.

6. The method according to claim 5, wherein the reagent for generating hydrogen peroxide from free glycerol is a reagent comprising glycerol kinase and glycerol 3-phosphate oxidase, or a reagent comprising glycerol oxidase.

7. The method according to claim 6, wherein the measurement of hydrogen peroxide is performed by generating a dye by allowing a peroxidative substance and oxidative coloring-type chromogen to act on the hydrogen peroxide, and measuring the absorbance of the dye.

* * * * *